(12) United States Patent
Pitman

(10) Patent No.: US 10,456,592 B2
(45) Date of Patent: *Oct. 29, 2019

(54) BRACHYTHERAPY FIDUCIAL NEEDLE FIXATION SYSTEM

(71) Applicant: Breast Microseed, Inc., Mercer Island, WA (US)

(72) Inventor: Charlie Pitman, Santa Barbara, CA (US)

(73) Assignee: BREAST MICROSEED, INC., Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/657,043

(22) Filed: Jul. 21, 2017

(65) Prior Publication Data

US 2017/0319871 A1 Nov. 9, 2017

Related U.S. Application Data

(63) Continuation of application No. 14/313,978, filed on Jun. 24, 2014, which is a continuation of application
(Continued)

(51) Int. Cl.
*A61N 5/10* (2006.01)
*A61B 17/34* (2006.01)
(Continued)

(52) U.S. Cl.
CPC ............ *A61N 5/1007* (2013.01); *A61B 5/061* (2013.01); *A61B 8/0841* (2013.01); *A61B 17/3403* (2013.01); *A61B 90/39* (2016.02);
*A61N 5/1015* (2013.01); *A61N 5/1049* (2013.01); *A61B 2017/3411* (2013.01);
(Continued)

(58) Field of Classification Search
CPC ...... A61N 5/10; A61N 5/1001; A61N 5/1002; A61N 5/1007; A61N 5/1014; A61N 5/1027; A61N 5/1028; A61N 2005/1008; A61N 2005/1009; A61N 2005/1011; A61N 2005/1012; A61N 2005/1023; A61N 2005/1024
See application file for complete search history.

(56) References Cited

U.S. PATENT DOCUMENTS

| 4,815,449 A | 3/1989 | Horowitz |
| 5,759,154 A | 6/1998 | Hoyns |

(Continued)

FOREIGN PATENT DOCUMENTS

| CN | 101198287 A | 6/2008 |
| WO | WO 01/72202 | 10/2001 |
| WO | WO 2004/014215 | 2/2004 |

OTHER PUBLICATIONS

TW Application No. 99112521, Official Letter dated Jan. 28, 2013 (11 pages).
(Continued)

*Primary Examiner* — Carrie R Dorna
(74) *Attorney, Agent, or Firm* — DLA Piper LLP (US)

(57) ABSTRACT

A mechanism facilitates the insertion of radioactive sources/source strands into soft tissue, such as breast tissue, that improves the reproducibility of the procedure and ensures that the sources are reliably and consistently inserted in an exact position per a patient prescription treatment plan from patient to patient as well as improve the ease-of-use of the device and procedure.

12 Claims, 33 Drawing Sheets

Related U.S. Application Data

No. 12/427,667, filed on Apr. 21, 2009, now Pat. No. 8,764,619.

(51) Int. Cl.
*A61B 5/06* (2006.01)
*A61B 8/08* (2006.01)
*A61B 90/00* (2016.01)

(52) U.S. Cl.
CPC ............ *A61B 2090/3908* (2016.02); *A61B 2090/3925* (2016.02); *A61B 2090/3991* (2016.02); *A61N 5/1027* (2013.01); *A61N 2005/1012* (2013.01)

(56) References Cited

U.S. PATENT DOCUMENTS

| | | | |
|---|---|---|---|
| 5,961,527 | A | 10/1999 | Whitmore et al. |
| 5,961,529 | A | 10/1999 | Arnold |
| 6,095,967 | A | 8/2000 | Black et al. |
| 6,508,786 | B2 | 1/2003 | Huitema et al. |
| 6,547,782 | B1 | 4/2003 | Taylor |
| 6,549,802 | B2 | 4/2003 | Thornton |
| 6,579,262 | B1 | 6/2003 | Mick et al. |
| 6,752,753 | B1 | 6/2004 | Hoskins et al. |
| 2004/0116767 | A1 | 6/2004 | Lebovic et al. |
| 2007/0021642 | A1 | 1/2007 | Lamoureux et al. |
| 2007/0043291 | A1 | 2/2007 | Fidel et al. |
| 2007/0265486 | A1 | 11/2007 | Van |
| 2007/0265487 | A1 | 11/2007 | Lamoureux et al. |
| 2009/0099402 | A1 | 4/2009 | Lamoureux et al. |

OTHER PUBLICATIONS

EP Application No. 10767725.4 Extended Search Report dated Aug. 23, 2012 (6 pages).
PCT/US2010/031937 International Search Report and Written Opinion dated Jun. 16, 2010 (10 pages).
Pignol, M.D., "First Report of a Permanent Breast PD Seed Implant as Adjuvant Radiation Treatment for Early-Stage Breast Cancer", Clinical Investigation, 2006 (6 pages).

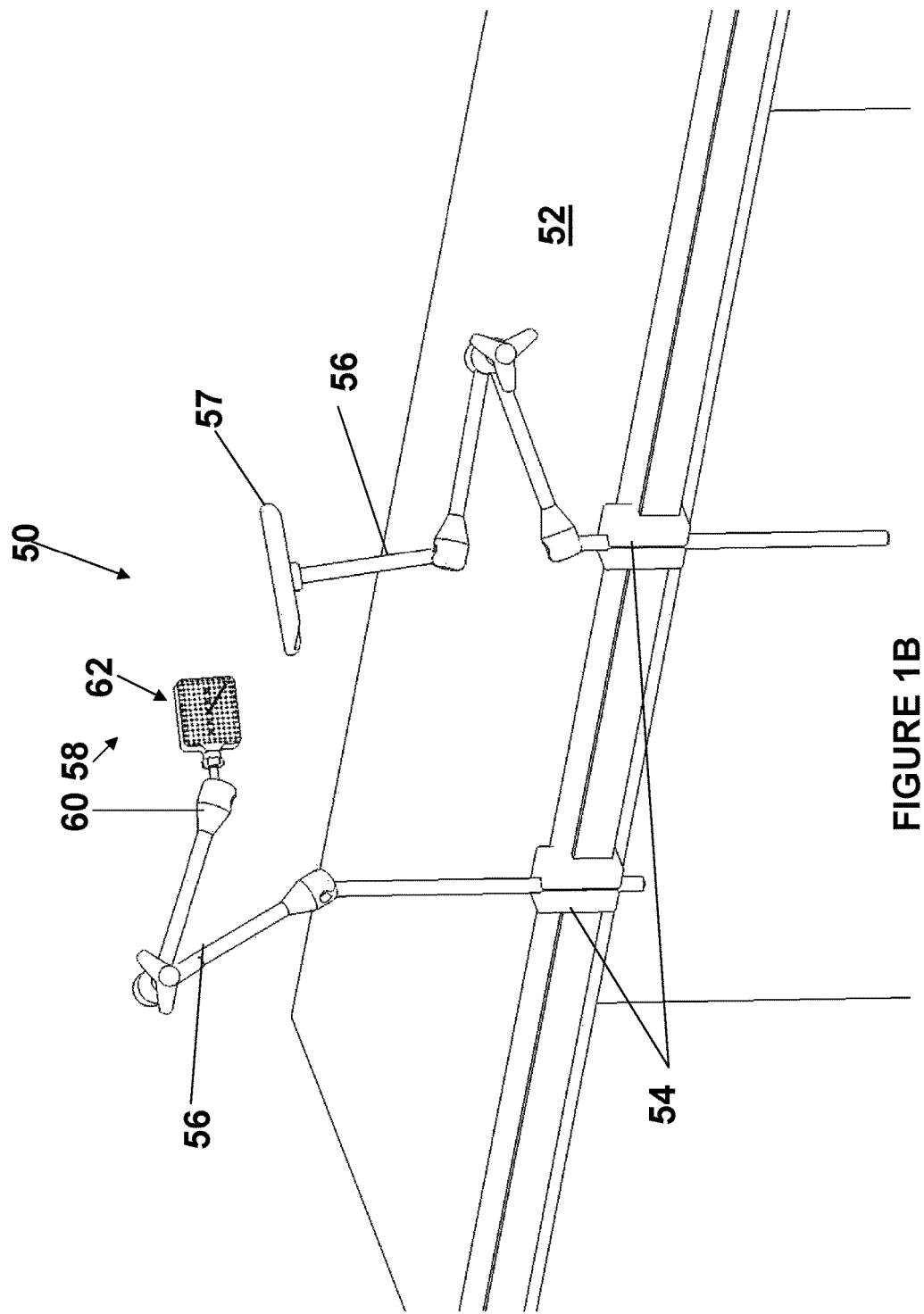

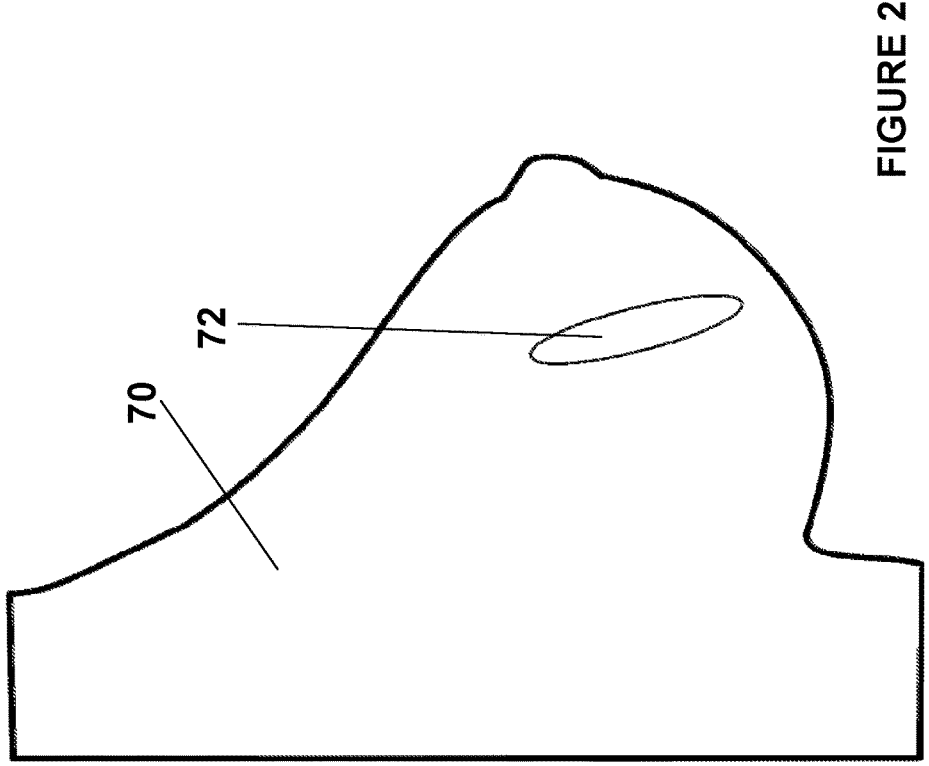

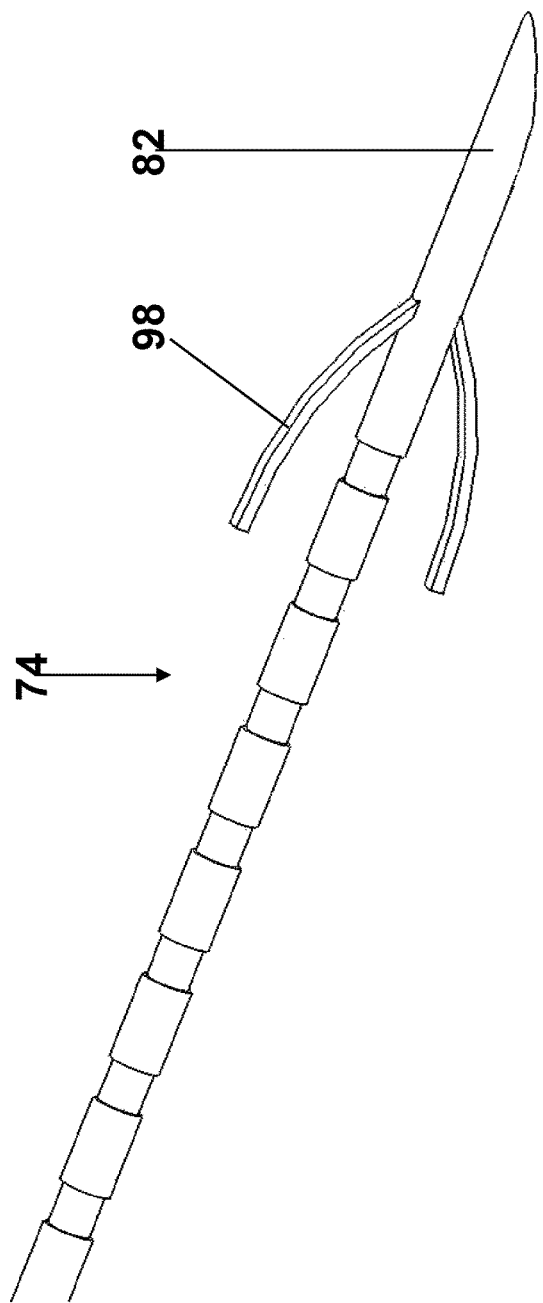

BRACHYTHERAPY FIDUCIAL NEEDLE FIXATION SYSTEM

PRIORITY CLAIMS/RELATED APPLICATIONS

This application claims priority under 35 USC 120 and is a continuation patent application of U.S. patent application Ser. No. 14/313,978, filed Jun. 24, 2014 and entitled "Brachytherapy Fiducial Needle Fixation System And Method" which in turn claims priority under 35 USC 120 and 121 and is a divisional patent application of U.S. patent application Ser. No. 12/427,667, filed on Apr. 21, 2009 and entitled "Brachytherapy Fiducial Needle Fixation System and Method", the entirety of all of which are incorporated herein by reference.

FIELD

The disclosure relates generally to a mechanism and method for radiation oncology.

BACKGROUND

When women are treated for breast cancer (which is the most commonly diagnosed cancer in women), they can opt for a mastectomy (complete removal of the breast tissue) or a breast conservation surgery. Due to the use of widespread screening mammograms, women are diagnosed with localized and early-stage disease so that the breast conservation surgery followed by radiation treatment may be used. The typical radiation treatment is adjuvant breast radiation. While the adjuvant breast radiation results in good survival rates, adjuvant breast radiation treatment typically takes 3.5 to 7 weeks which is too long. In addition, since the adjuvant breast radiation treatment is typically provided using external beam radiation, there is a greater risk of acute skin reactions due to the healthy tissue interaction with the radiation.

As a result, accelerated partial breast irradiation may be used which results in a quicker treatment time and less radiation-induced acute skin reactions. One technique used for the accelerated partial breast irradiation is brachytherapy. In one method, radioactive sources are permanently implanted into the breast tissue at the site of the surgery wherein the radioactive sources may be high dose or low dose.

Currently there are a handful of ways to insert radioactive sources into breast tissue. One is by a free hand method, another uses a compressive template device to temporary hold insertion catheters and the last uses a locking template system and non-fixated fiducial needle. These methods are limited in that they do not ensure the sources are placed in the desired location as prescribed by the treatment plan 100% of the time. The lack of ability to place the radioactive sources in the desired location means that the remaining tumor margin is not receiving the appropriate radiation and healthy tissue is receiving unwanted radiation.

In the high dose rate brachytherapy area, a clinician would place hollow catheters into the breast to facilitate the insertion of a temporary radioactive source per a treatment plan which are then removed once the treatment is completed. The placement of these catheters may be by either free hand directly into the breast or by free hand though compressive template systems used to stereo-tactically immobilize the breast. Both Varian Medical Systems and Nucletron offer commercially available template immobilization products.

In the low dose rate brachytherapy area, one method for permanent breast radioactive seed implantation is described in detail in "First Report of a Permanent Breast[103]PD Seed Implant As Adjuvant Radiation Treatment for Early-Stage Breast Cancer", Dr. Jean-Philippe Pignol et al., International Journal of Radiation Oncology Biological Physics, Vol. 64, No. 1, pp. 176-181 (2006) which is incorporated herein by reference. This method uses a non-fixated fiducial needle, locking template and stereotactic fixation to insert lose dose rate (LDR) radioactive source strands into the treatment site. In this method, the fiducial needle can migrate/move once inserted thus changing the depth at which the source strands are deployed. In addition, the system is very cumbersome to use and is not user intuitive.

Thus, it is desirable to provide a mechanism to facilitate the insertion of radioactive sources/source strands into soft tissue, such as breast tissue and a method that utilizes this mechanism with the goal of improving the reproducibility of the procedure and ensuring that the sources are reliably and consistently inserted in an exact position per a patient prescription treatment plan from patient to patient as well as improve the ease-of-use of the device and procedure. It is to this end that the disclosure is directed.

BRIEF DESCRIPTION OF THE DRAWINGS

FIGS. 1A and 1B illustrate a mechanism for adjuvant partial breast irradiation;

FIG. 2 illustrates a view of a breast with a tumor;

FIGS. 6A-6I illustrates examples of a fiducial needle with a retention device that may be used with the mechanism for adjuvant partial breast irradiation shown in FIGS. 1A and 1B;

DETAILED DESCRIPTION OF ONE OR MORE EMBODIMENTS

The disclosure is particularly applicable to low dose radioactive source implantation into breast tissue and it is in this context that the disclosure will be described. It will be appreciated, however, that the mechanism and method has greater utility since the mechanism can be used to implant various different radioactive sources into various different tissues.

Figure 1A:
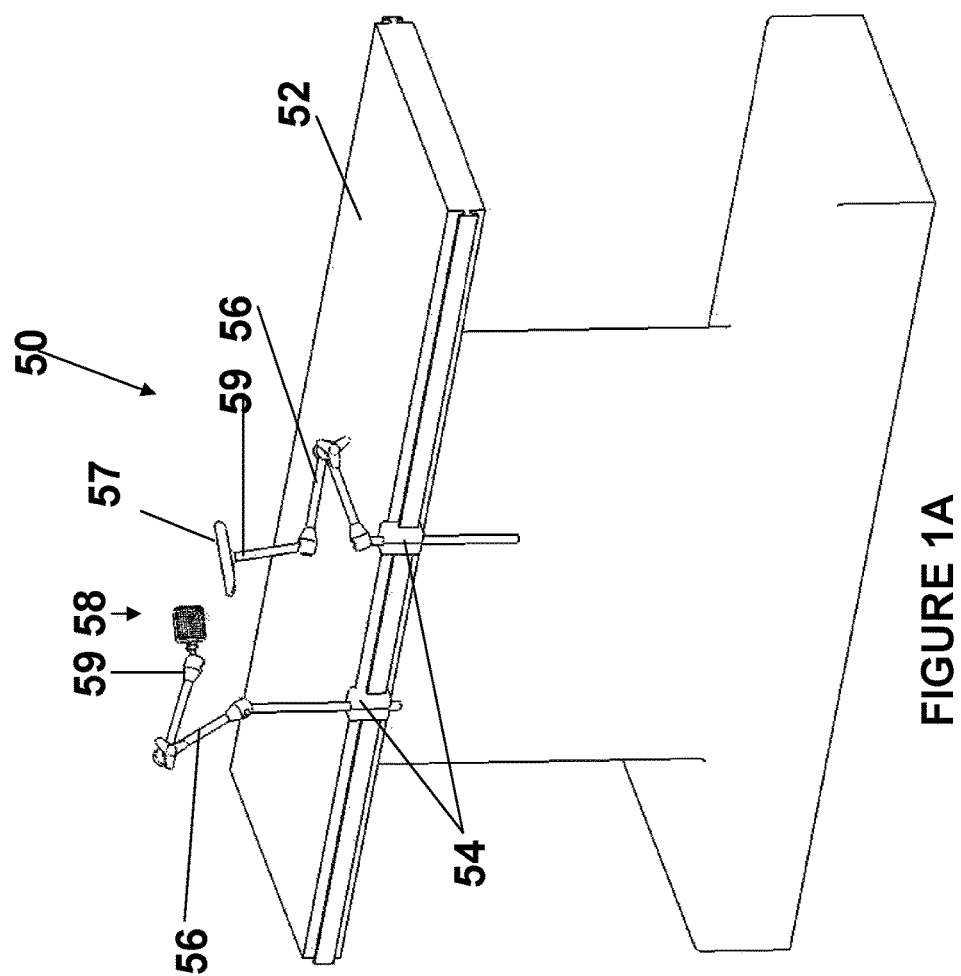

FIGS. 1A and 1B illustrate a mechanism 50 for adjuvant partial breast irradiation. The mechanism may include a table 52 on which a patient lies of their back to have the radioactive sources implanted into the surgery cavity in their breast tissue following breast conservation surgery. The mechanism may also include one or more well-known table clamps 54 that are used to clamp one or more stereotactic armatures 56 to the table and fix the stereotactic armatures relative to the table. Each stereotactic armature 56 may have joints that allow the position of an operational end 59 of the armature to be adjusted and then fixed relative to the table in three dimensions to form a fixed frame of reference. The mechanism may further include a needle retraction stop 57 attached to one stereotactic armature 56 and a fiducial needle fixation assembly 58 attached to another stereotactic armature 56 to form the fixed frame of reference.

Figure 3:
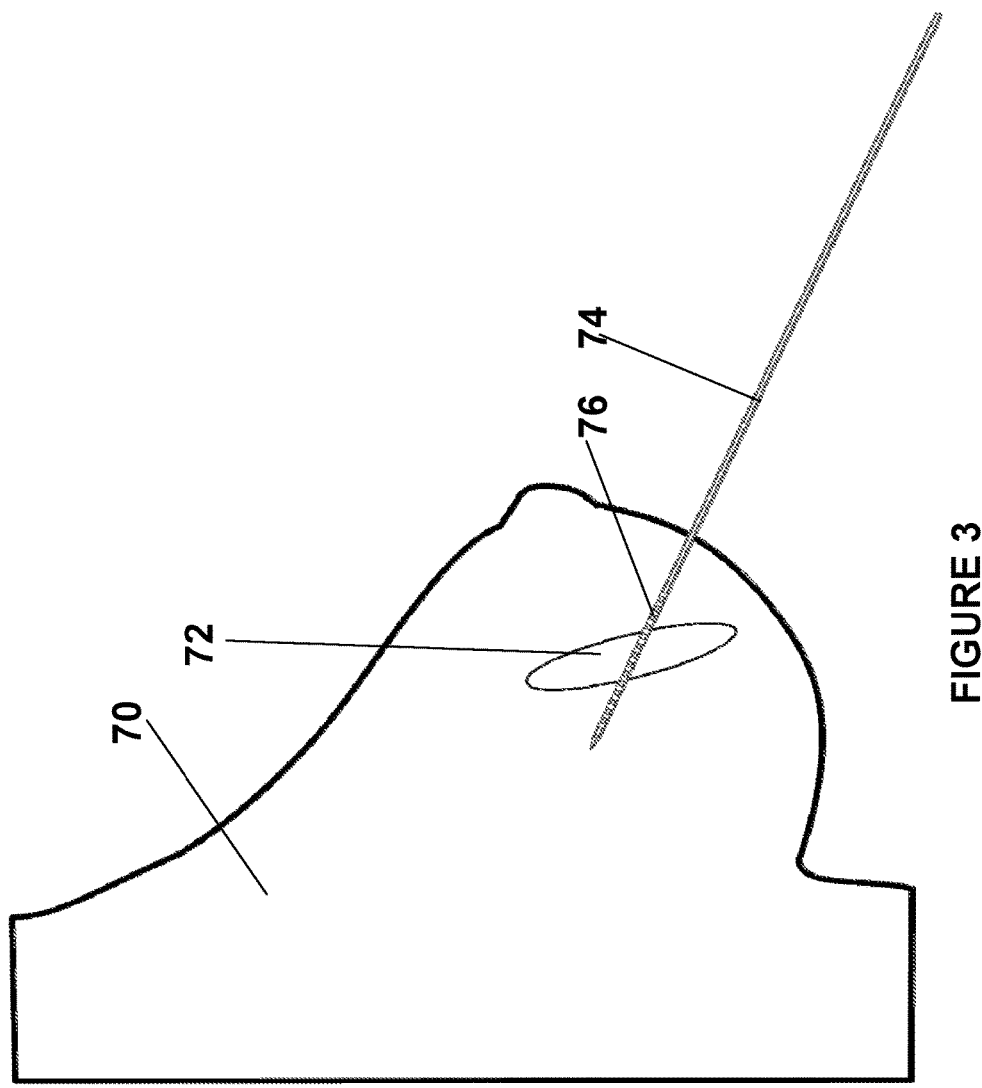
FIG. 3 illustrates a view of a breast with a tumor with a fiducial needle inserted to accurately locate the tumor.

As shown in FIG. 1B, the fiducial needle fixation assembly 58 may further include an engagement device 60 that allows a fiducial needle fixation device 62 to be quickly and securely removably fixed to the stereotactic armature 56. Generally, the patient may lie on the table with the breast tissue against the fiducial needle fixation assembly 58 so that one or more fiducial needles may be inserted into the breast tissue and the surgery cavity using an electromagnetic imaging system, such as for example ultrasound so that the surgeon can then accurately place the one or more radioactive sources into the tumor bed/surgery cavity using an electromagnetic imaging system, such as for example ultrasound to visualize the tumor bed/surgery cavity due to the one or more fiducial needles as described below in more detail. In one implementation, the one or more radioactive sources may be $^{103}$PD seeds and/or seed strands. The radioactive seeds may also be $^{125}$I and or $^{131}$Cs FIG. 2 illustrates a view of a breast 70 with a lumpectory site after the surgical removal of the tumor 72 (or surgery cavity when the majority of the tumor has been removed during breast conservation surgery) and FIG. 3 illustrates a view of the breast 70 with the tumor/surgery cavity 72 with a fiducial needle 74 inserted to accurately locate the tumor/surgery cavity to allow the precise placement of the radioactive sources according to the treatment plan. In a process to place one or more radioactive sources into the breast tissue/surgery cavity following the breast conservation surgery, there may be one or more fiducial needles 74 inserted although only one fiducial needle 74 is shown in FIG. 3 for illustration purposes. As described below, each fiducial needle 74 may have one or more visualization features 76 (described in more detail below with respect to FIGS. 4A and 4B) that can be seen when an electromagnetic source irradiates the breast tissue so that, based on the fiducial needles, the one or more radioactive sources can be precisely placed into the breast tissue according to a treatment plan to kill any tumor cells that were not removed during the breast conservation surgery.

Figure 4A:
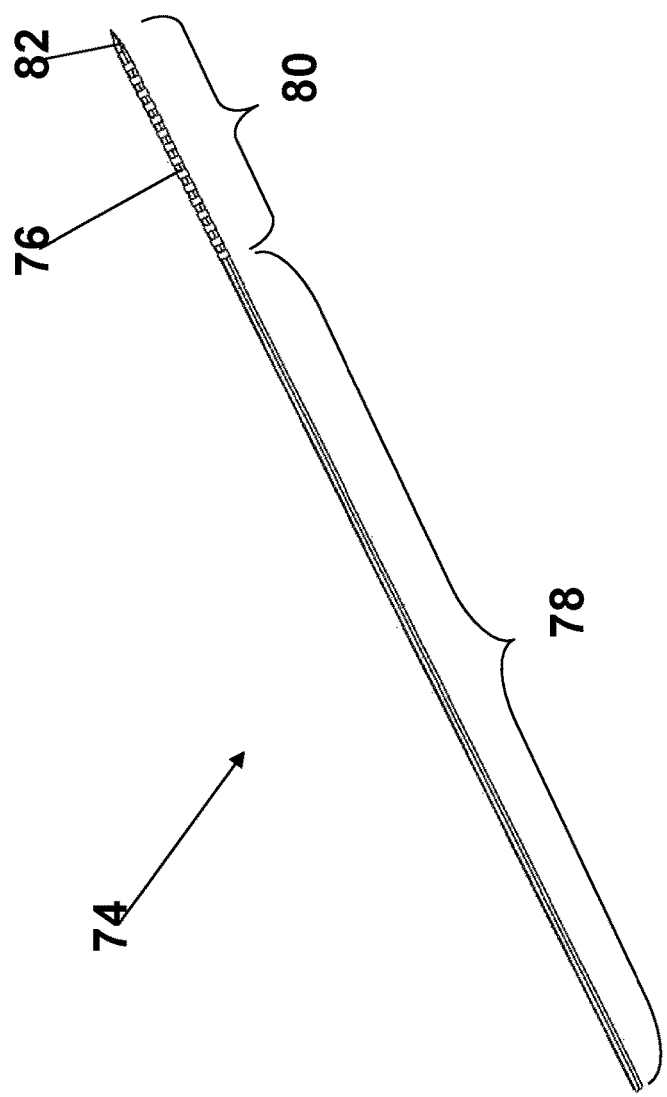
FIGS. 4A and 4B illustrate an example of a fiducial needle that can be used with the mechanism for adjuvant partial breast irradiation shown in FIGS. 1A and 1B.
Figure 4B:
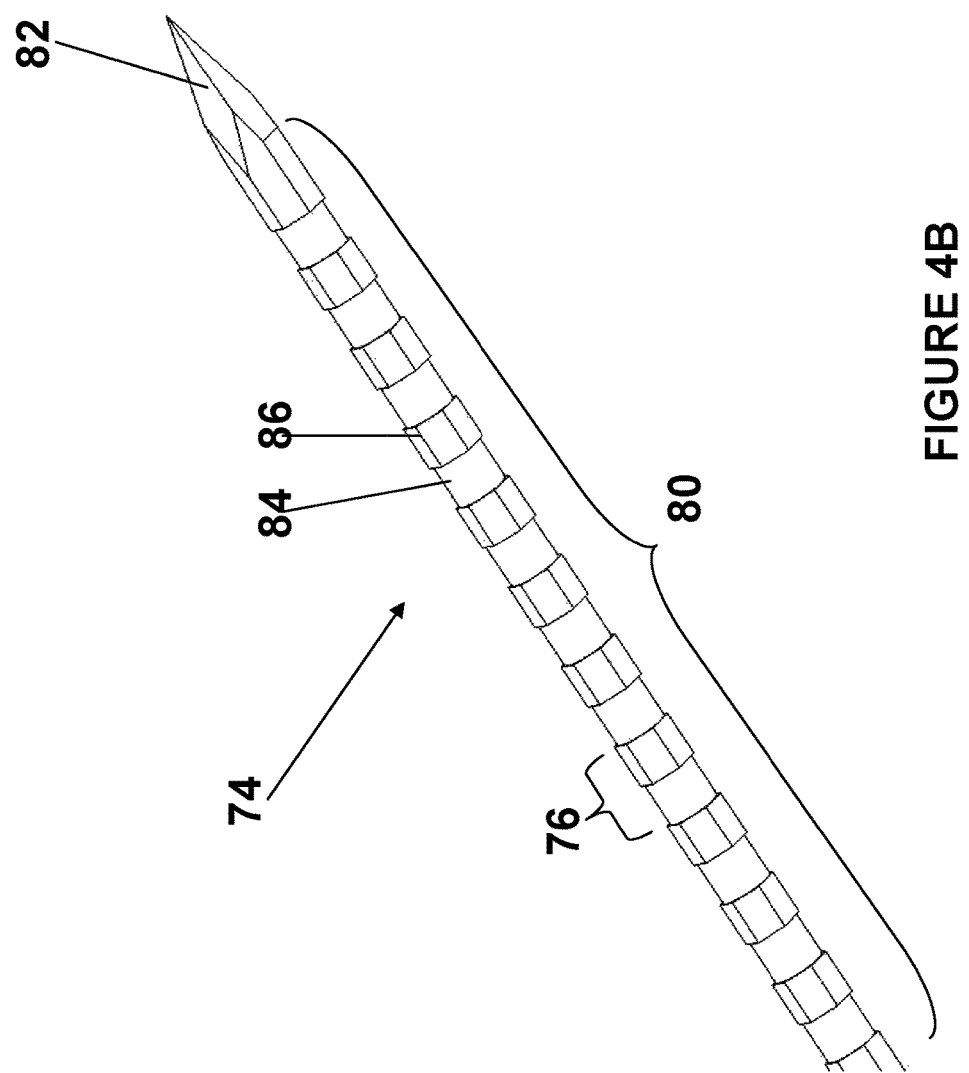
Figure 4C:
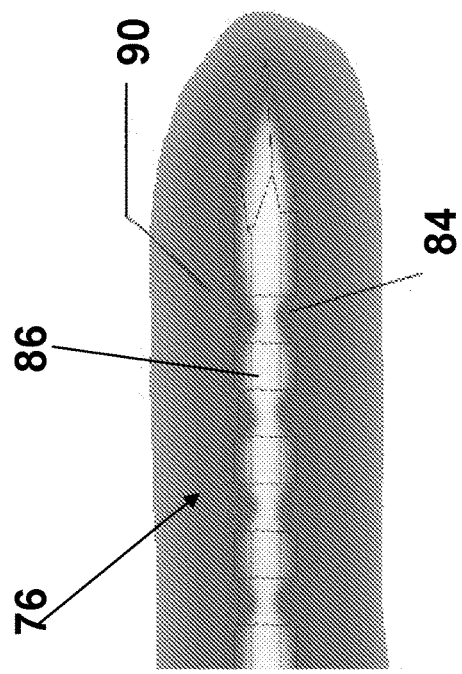
FIG. 4C illustrates one technique for fiducial needle fixation.

FIGS. 4A and 4B illustrate an example of a fiducial needle 74 that can be used with the mechanism for adjuvant partial breast irradiation shown in FIGS. 1A and 1B. Each fiducial needle used in the adjuvant partial breast irradiation shown in FIGS. 1A and 1B may have a shaft portion 78, a visualization portion 80 that has the one or more visualization features 76 and a tip portion 82. The fiducial needle may be constructed out of a rigid material and have an enhanced geometry that will facilitate its fixation in the breast tissue. The shaft portion may be constructed out of rod stock and may have a round, square, triangular, hexagonal or octagonal cross section. The fiducial needle may also have a retention features on the tip end that allows the needle to be easily inserted and removed but, once in place, fixate the needle in its location by either tissue encapsulation into features of the needle (as shown in FIG. 4C and described below) or by penetration by either a user deployable projection feature or similar structure as shown in FIGS. 6A-6I which are described below. In one implementation, the overall outside diameter of the needle shall be 15 gauge to 22 gauge (0.070" to 0.028") and the needle may have a length of 3" to 12". The needle may be manufactured out of stainless steel, stainless steel alloys including 304, 316/316L, 321, 347, Inconel 624, 17-7ph, 430/434, Hastelloy C-276, Invar36, and or a polymer based material. The needle may have a sharpened tip to facilitate easy penetration into tissue and the tip may be trocar, pencil and or beveled in its point geometry.

As shown in FIG. 4B, the geometry of the needle may be optimized to facilitate visualization with various clinical imaging modalities using the visualization features 76. Each visualization feature 76 may be geometry that is tailored to promote visualization under imaging. For example, each visualization feature 76 may further comprise topographic features of elevated or depressed surface characteristics towards the tip of the needle that will help reflect the energy from an imaging system so that the position and orientation of the feature 76 and the fiducial needle can be accurately determined using the imaging system. In one implementation, each visualization feature 76 may include a depressed region 84 adjacent to an elevated region 86 as shown in FIG. 4B.

FIG. 4C illustrates one technique for fiducial needle fixation into tissue 90. As shown in FIG. 4C, once the fiducial needle 74 is inserted into the tissue 90, the tissue may move into the depressed regions 84 (tissue encapsulation) which will cause the fiducial needle to be temporarily anchored into the tissue.

Figure 5:
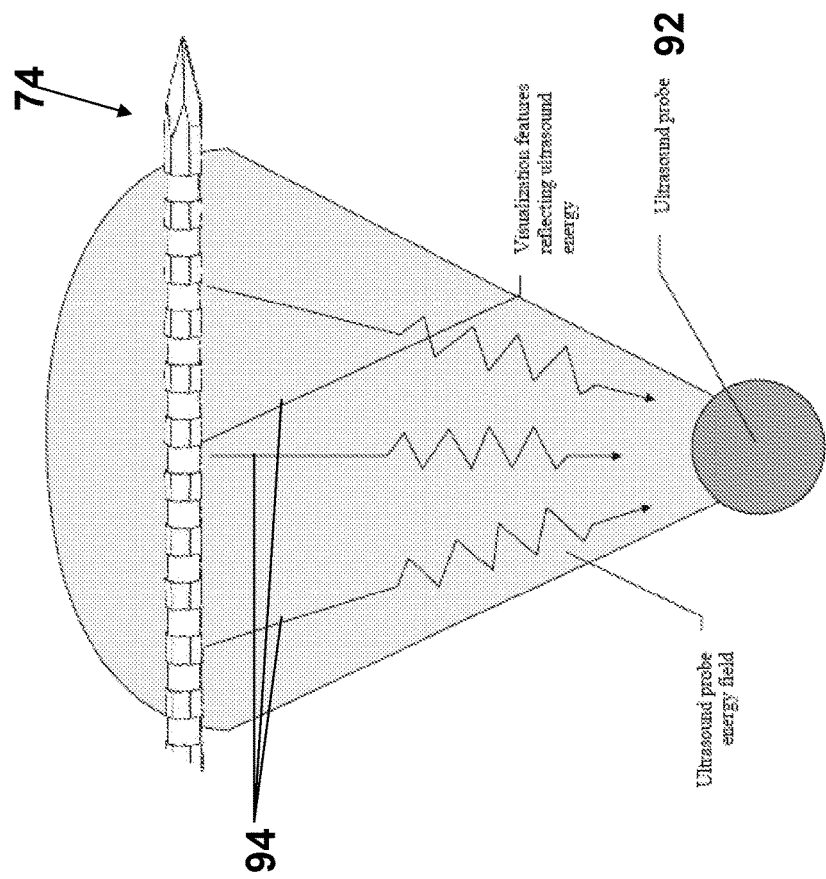
FIG. 5 illustrates using an electromagnetic device for visualizing the fiducial needle shown in FIGS. 4A and 4B.
Figure 6B:
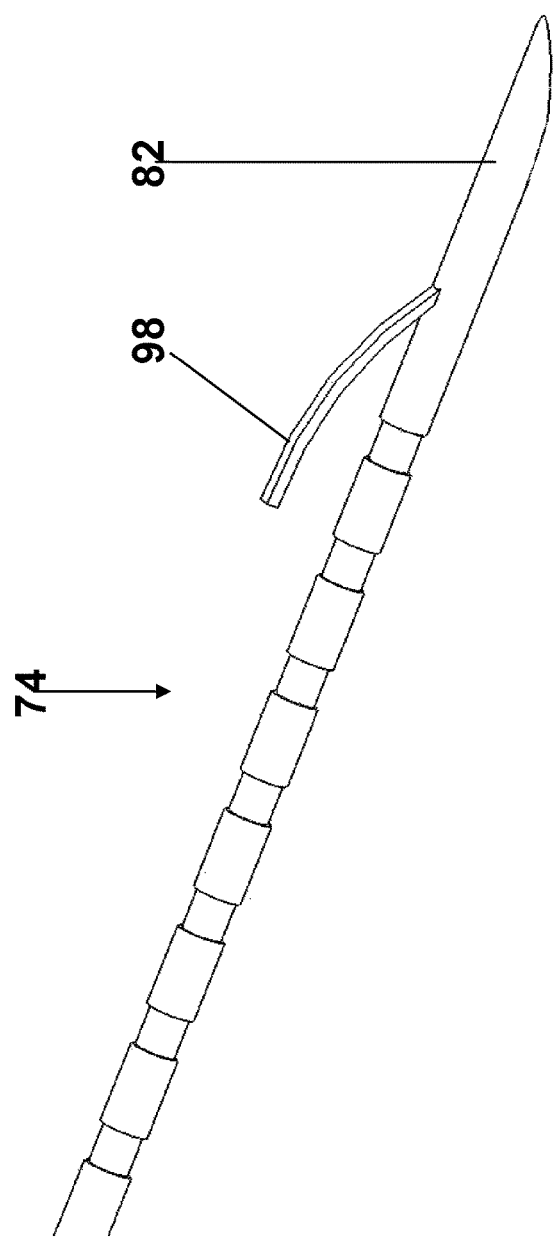
Figure 6C:
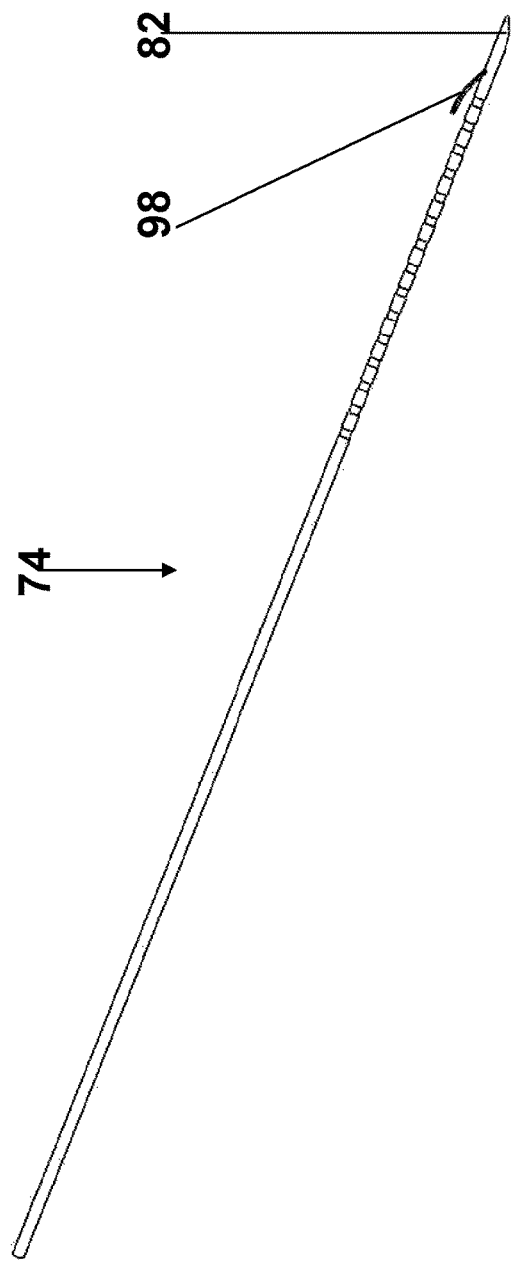
Figure 6D:
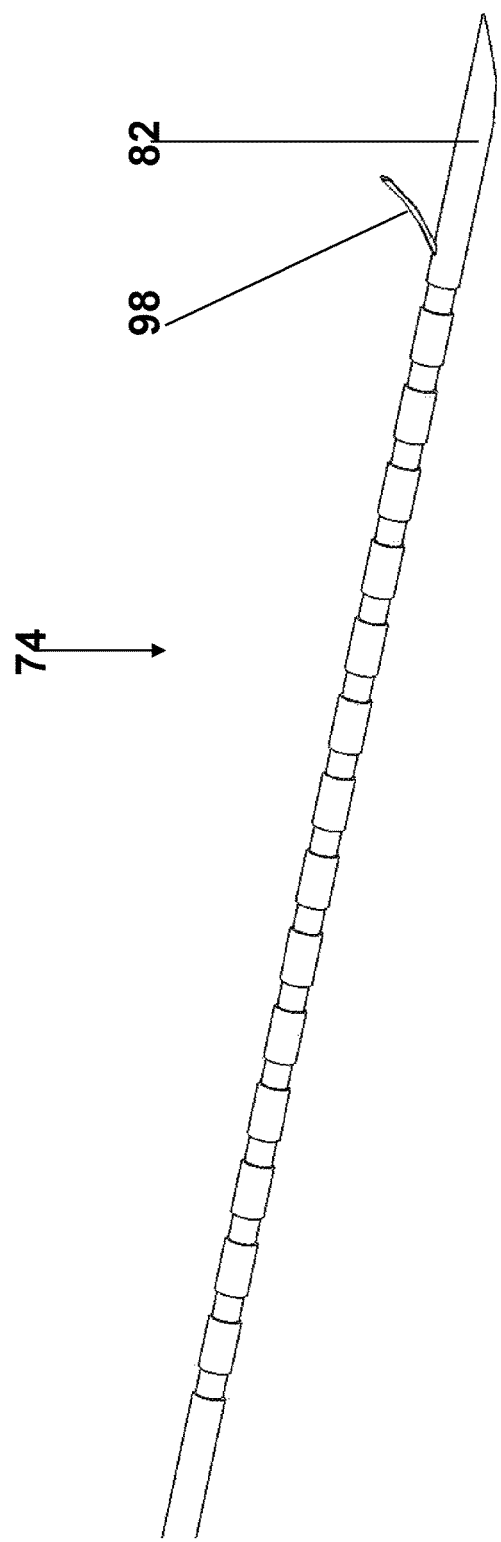
Figure 6E:
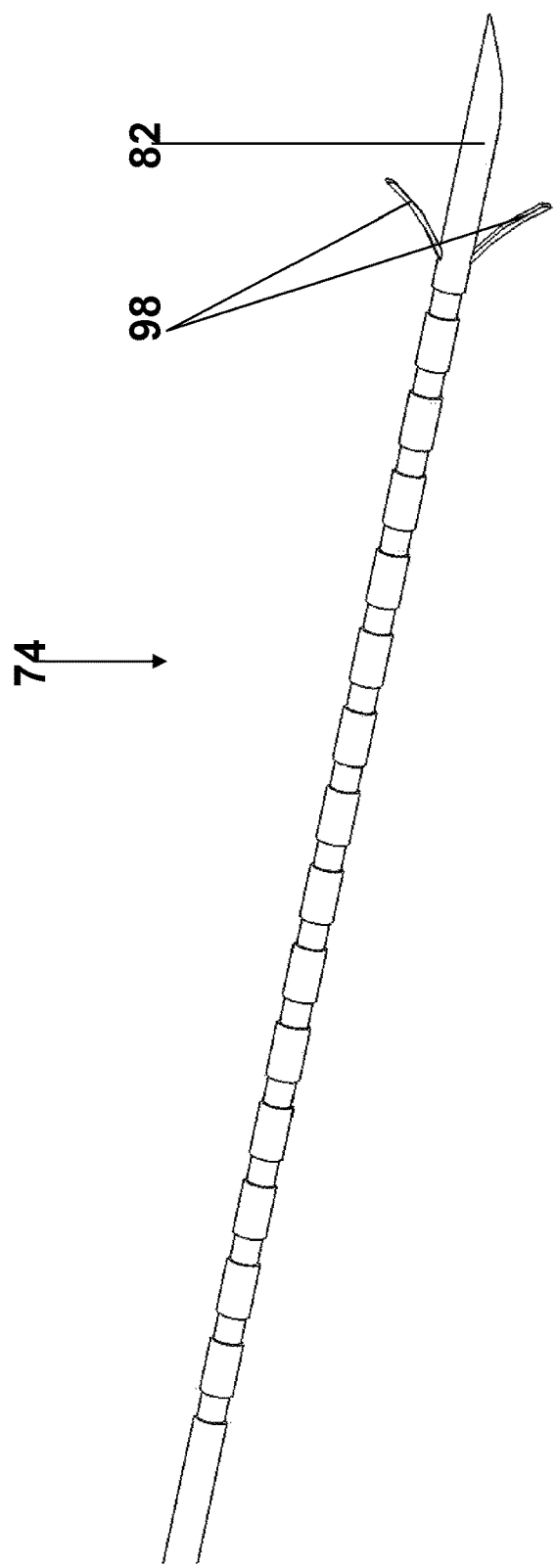
Figure 6F:
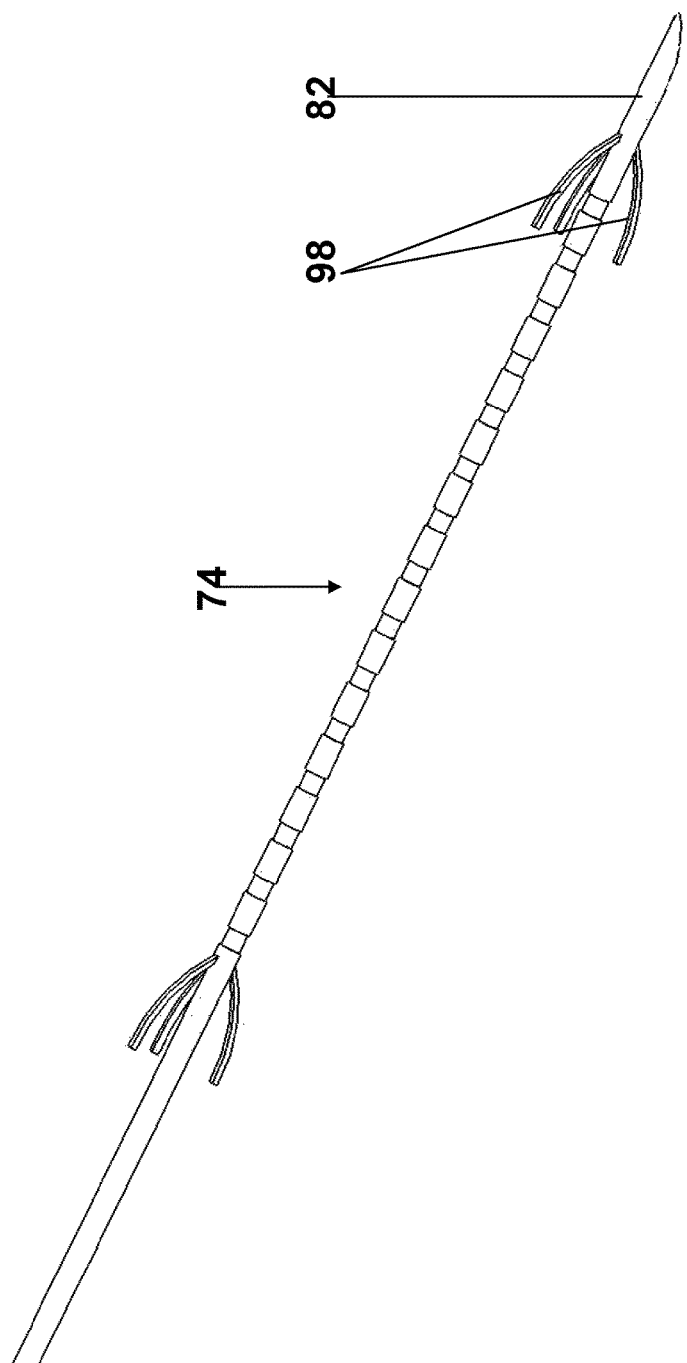
Figure 6G:
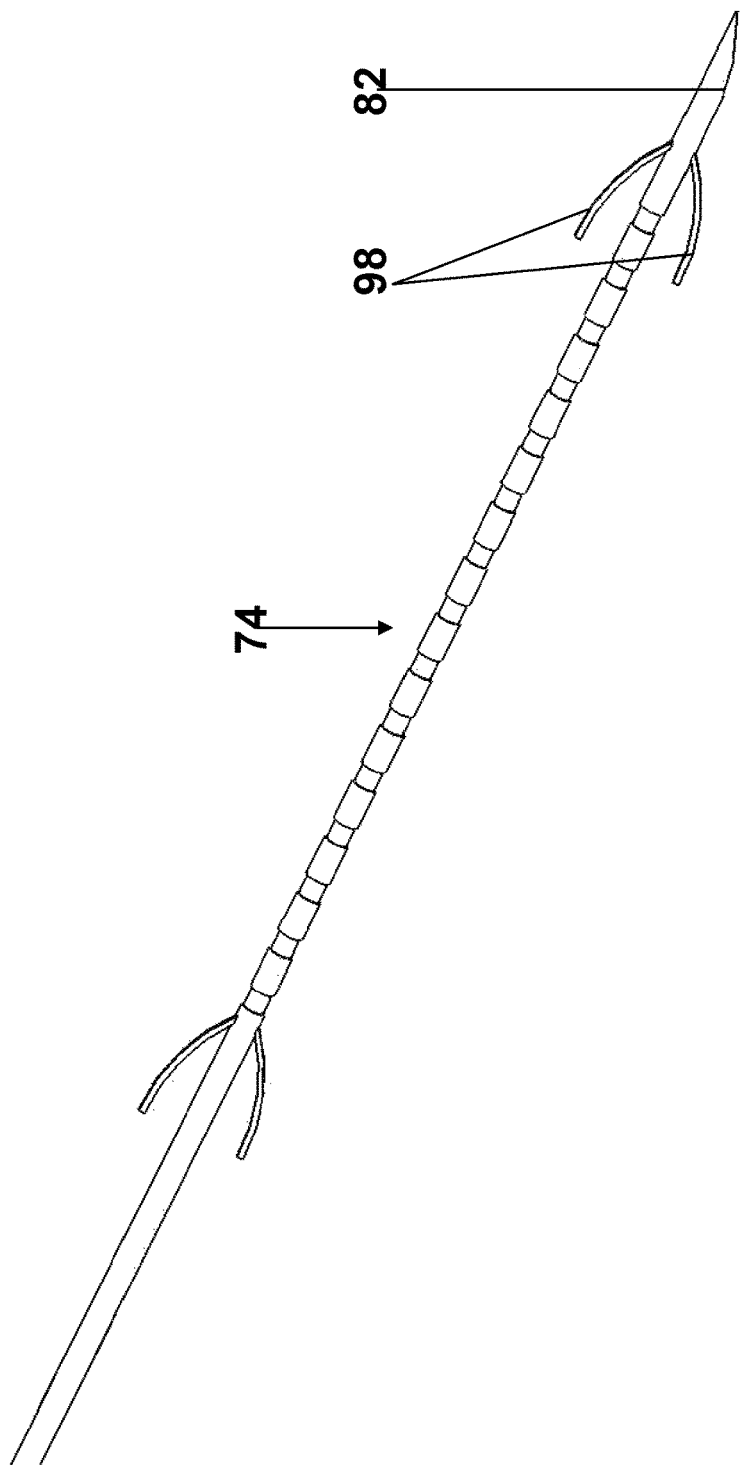
Figure 6H:
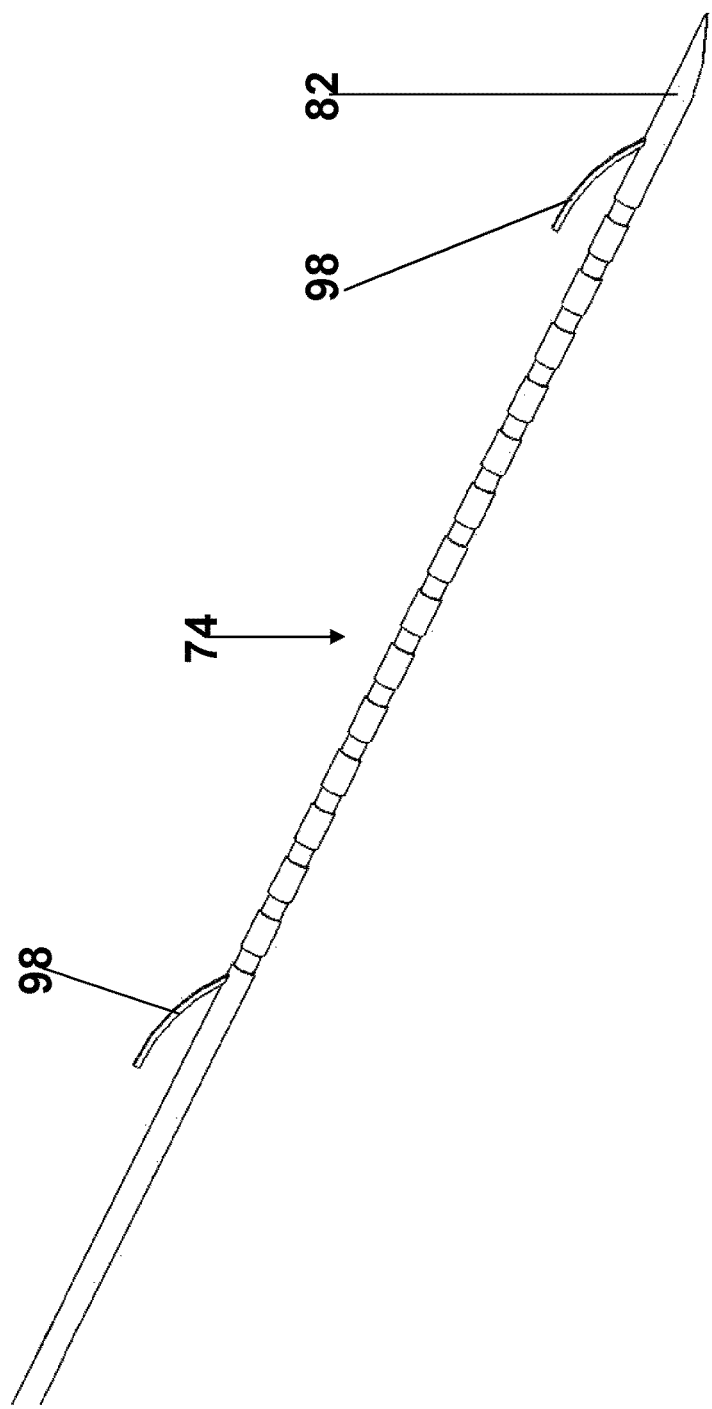
Figure 6I:
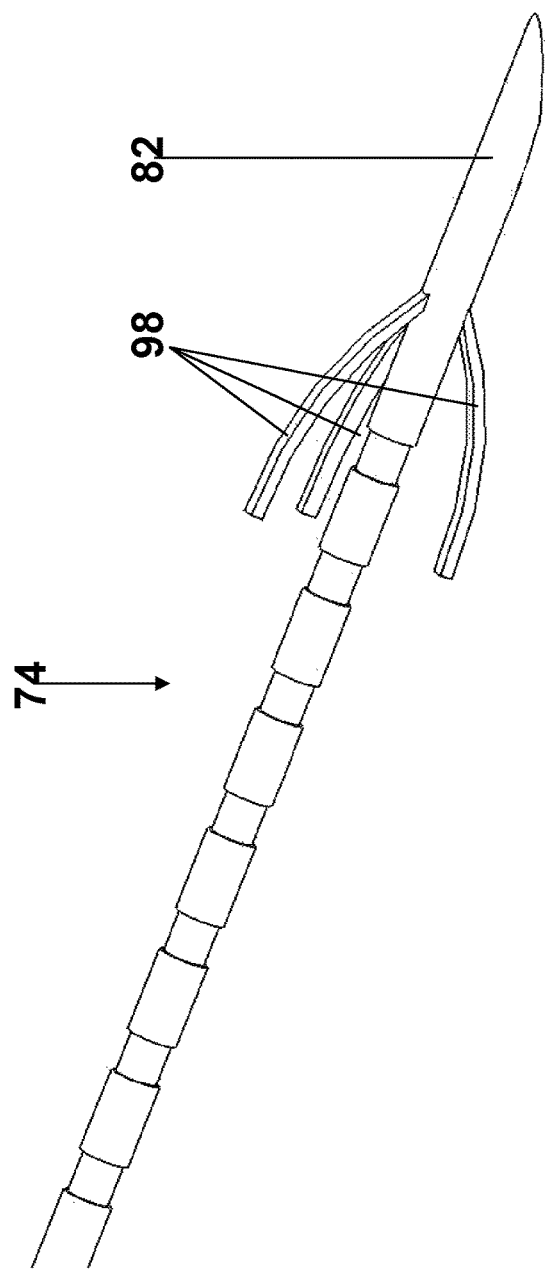

FIG. 5 illustrates using an electromagnetic device 92 for visualizing the fiducial needle 74 shown in FIGS. 4A and 4B. The electromagnetic device 92 may be an imaging device that generates electromagnetic energy. In one implementation, the electromagnetic device 92 may be an ultrasound imaging device. The electromagnetic device 92 may also be fluoroscopy, magnetic resonance imaging (MRI) and or computerized tomography (CT) As shown, the electromagnetic device 92 generates energy that strikes the needle 74 and is reflected by the features 76 of the needle as radiated energy 94 that is received by the electromagnetic device 92 in order to precisely determine the position and orientation of the needle 74 relative to the electromagnetic device 92 (and hence the precise position and orientation of the tumor/surgery cavity into which the radioactive sources may be implanted during the treatment.

FIGS. 6A-6I illustrates examples of a fiducial needle 74 with a retention device 98 that may be used with the mechanism for adjuvant partial breast irradiation shown in FIGS. 1A and 1B. These figures show a plurality of different examples of a retention device 100, such as a user deployable and retractable barb feature (a user deployable projection) that can be used to fixate the fiducial needle once it is positioned so that the position of the fiducial needle relative to the breast tissue and the mechanism shown in FIGS. 1A and 1B does not change during the procedure to insert the one or more radioactive sources into the breast tissue so that the position of the one or more radioactive sources is precisely controlled. Any of the different examples shown in these figures may also be combined together. Now, the fiducial needle fixation device 62 is described in more detail.

Figure 7:
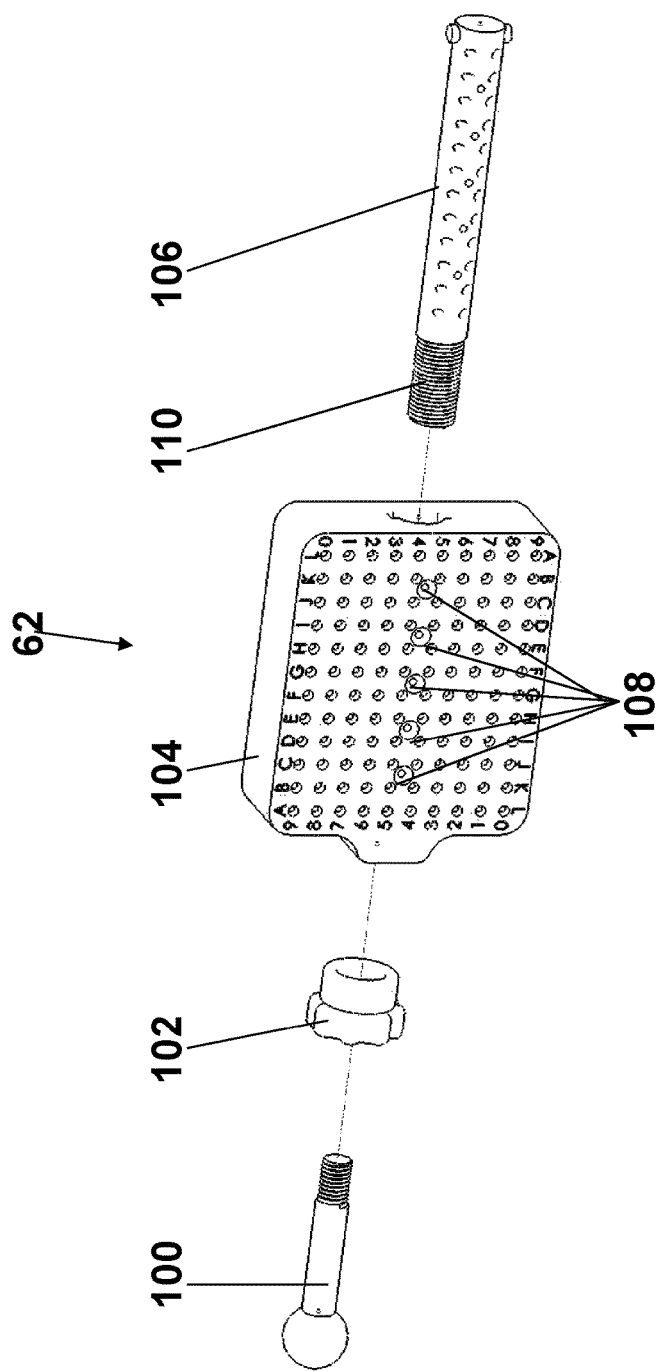
FIG. 7 illustrates an example of a fiducial needle fixation device that may be used with the mechanism for adjuvant partial breast irradiation shown in FIGS. 1A and 1B.

FIG. 7 illustrates an example of the fiducial needle fixation device 62 that may be used with the mechanism for adjuvant partial breast irradiation shown in FIGS. 1A and 1B. In one implementation, the fiducial needle fixation device 62 may comprise an attachment ball device 100, a fiducial needle lock 102, a template 104 and a locking pin 106 that when attached to each other, lock one or more fiducial needles into the template 104 and rigidly secure the template to the attachment ball device 100 which in turn is rigidly connected to the stereotactic armature. To lock the one or more fiducial needles into the template 104 at one or more fiducial needle locations 108 of the template, the one or more fiducial needles are inserted into the one or more fiducial needle locations 108 with the locking pin 106 in an unlocked position and then the fiducial needle lock 102 is tightened to a locked position using a set of threads 110 on the locking pin which causes the locking pin 106 to be pulled towards the fiducial needle lock 102 which moves the locking pin into a locking position as will be described below in more detail. Alternatively, the fiducial needle lock 102 may move from the unlocked position to the locked position using other mechanisms instead of the set of threads.

In the fiducial needle fixation device 62, the locking of the fiducial needles into a position does not affect any needles in the other holes of the template (holes A0-A9 through L0-L9) so that those needles (such as needles that deliver the radioactive sources into the treatment site) are not locked into a position. Once the fiducial needles are locked into position, the attachment ball device 100 may be screwed into an inner set of threads of the locking pin (as shown in FIG. 9B) to provide a rigid but alterable attachment of the template to the attachment ball device 100 so that the attachment ball device may be inserted into the engagement device 60 of the mechanism as shown in FIGS. 1A and 1B. Alternatively, the attachment ball device 100 may be attached to the fiducial needle fixation device 62 by a locking mechanism instead of the set of threads.

Figure 8:
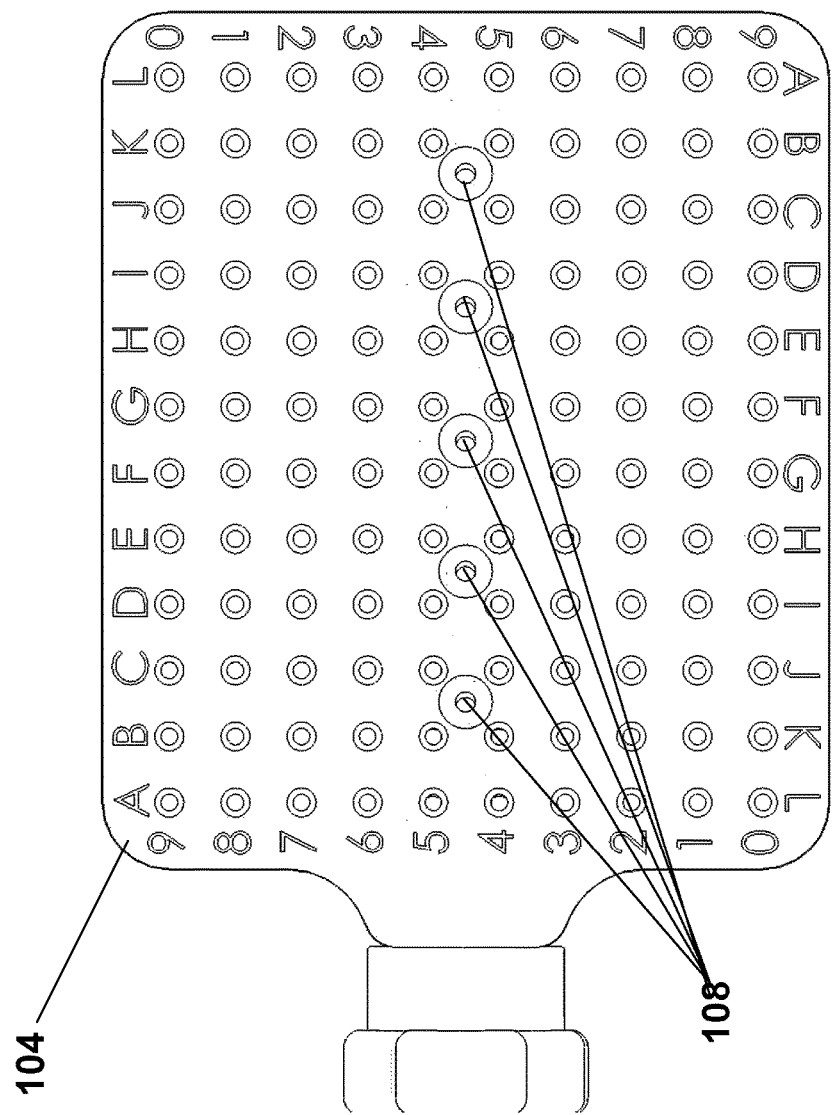
FIG. 8 illustrate more details of the template shown in FIG. 7.

FIG. 8 illustrate more details of the template 104 shown in FIG. 7. In one example, the template is a solid/hollow rectangular shaped piece of material (although the template can be other shapes and sizes to accommodate differing tumor/patient sizes) that has the lockable fiducial needle locations 108 as well as the other needle holes that are not lockable as described above. Once the one or more fiducial needles are locked into position and the fiducial needle fixation device 62 is locked into position relative to the mechanism 50, the needles with the radioactive sources can be inserted into the template holes at precisely known locations to insert and implant the radioactive sources into the breast tissue according to the coordinated locations of the prescription treatment plan.

Figure 9A:
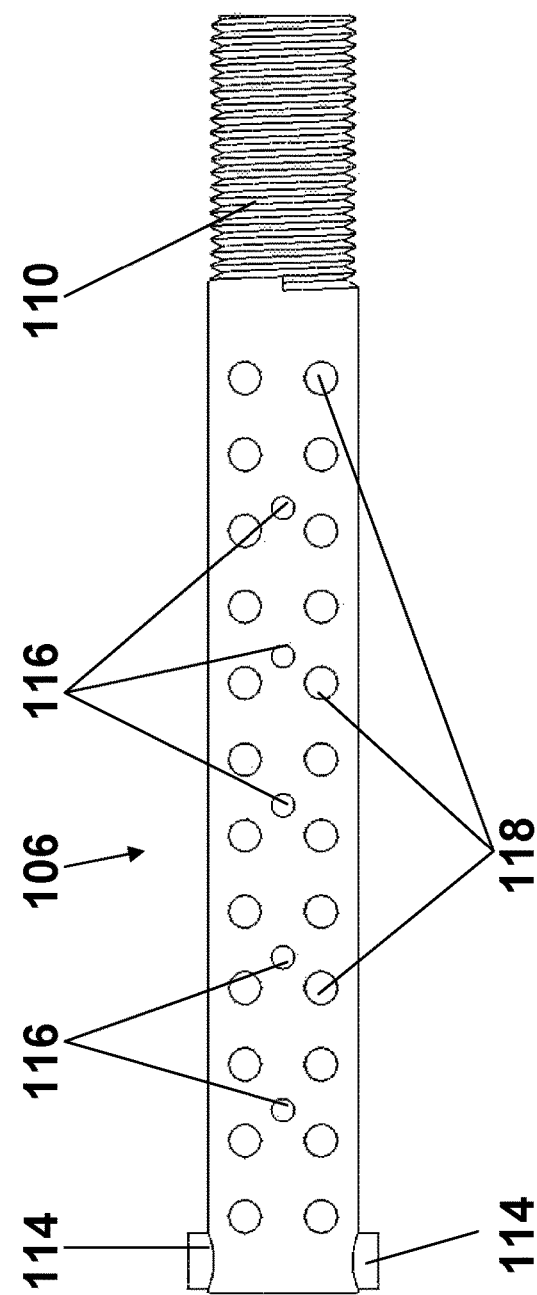
FIGS. 9A and 9B illustrate an example of a locking pin of the template shown in FIGS. 7 and 8.
Figure 9B:
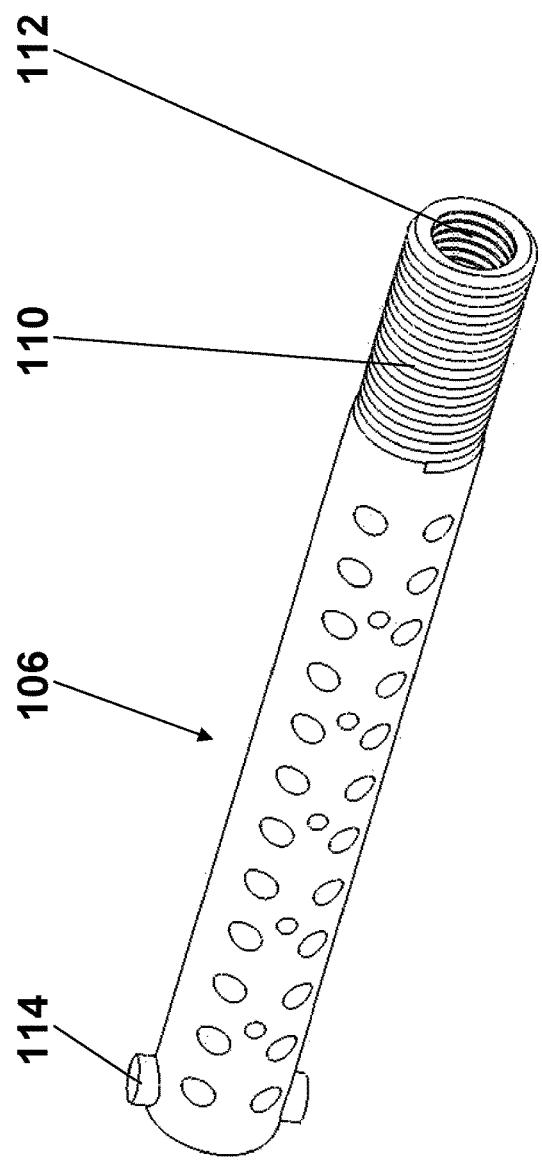
Figure 10:
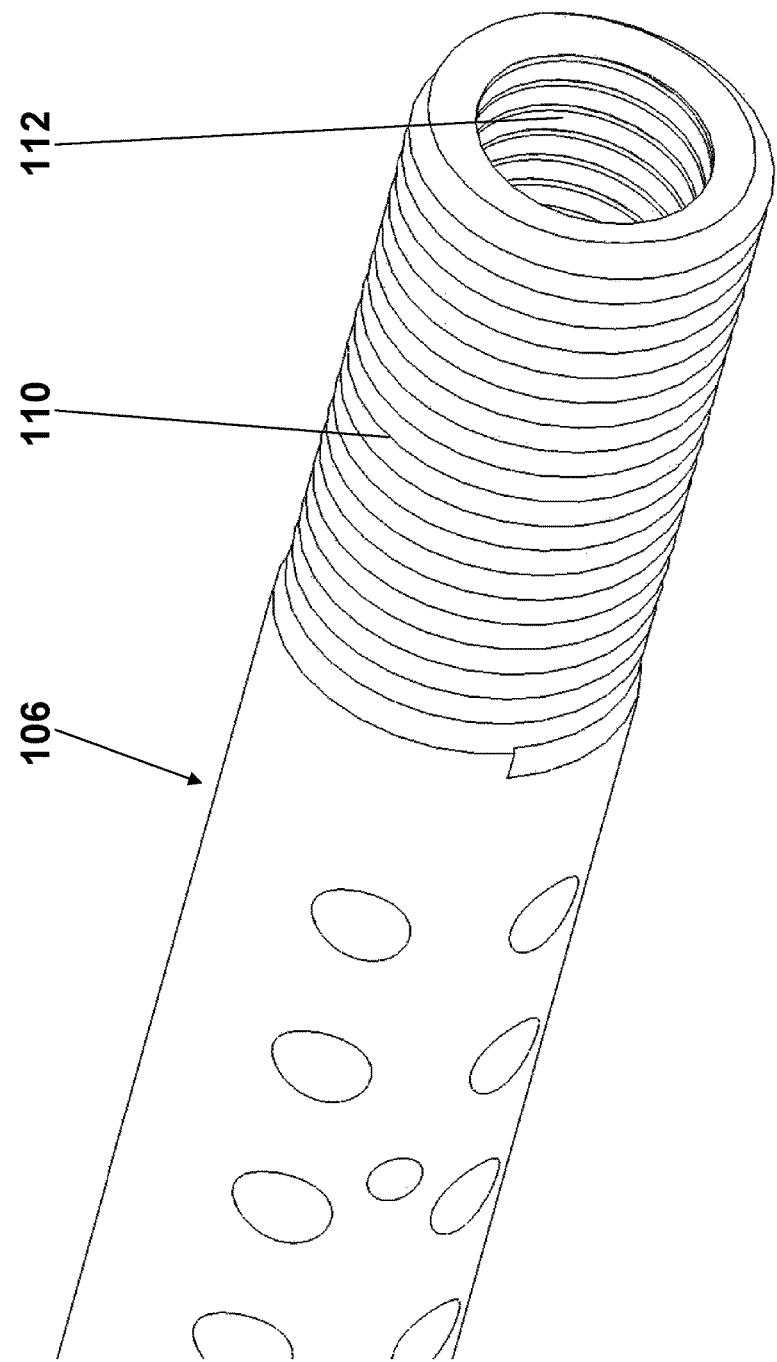
FIG. 10 illustrate more details the locking pin shown in FIGS. 9A and 9B.
Figure 11:
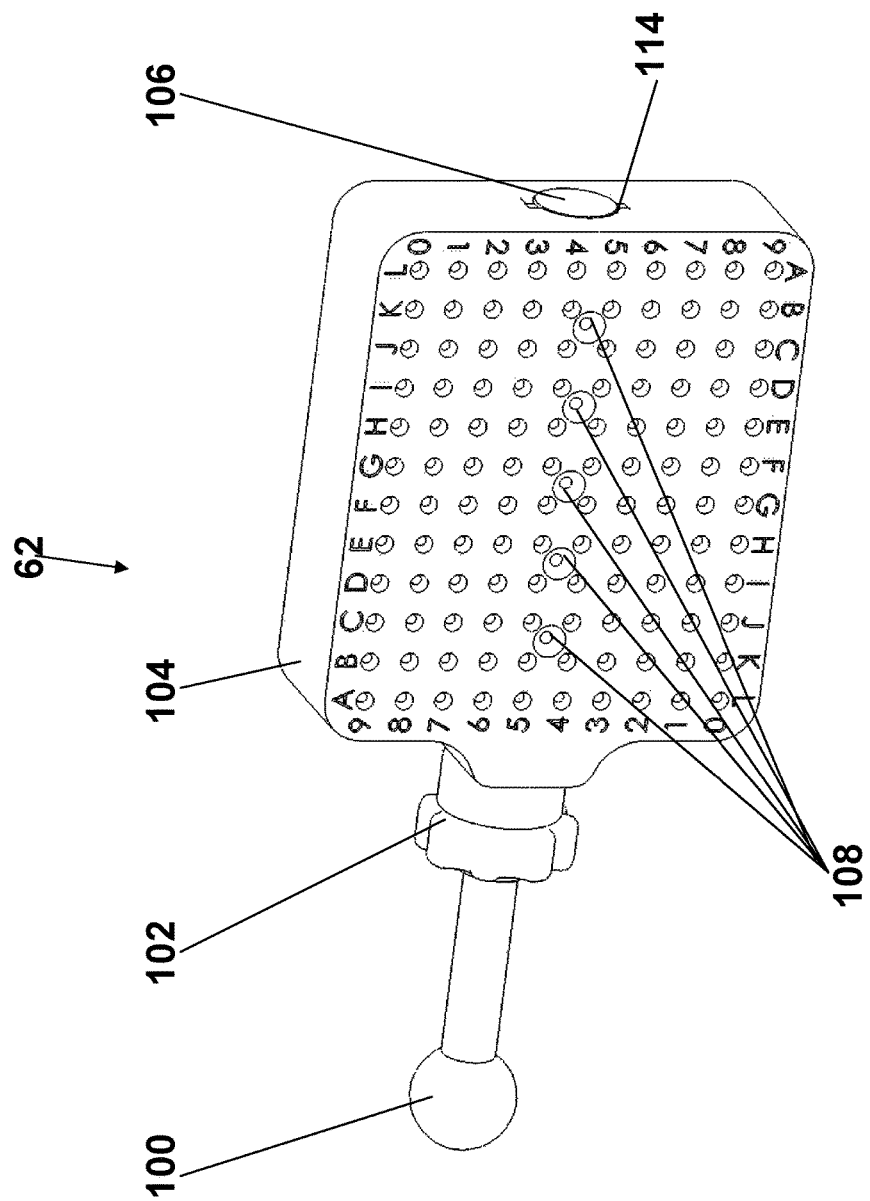
FIG. 11 illustrates an assembled fiducial needle fixation device that may be used with the mechanism for adjuvant partial breast irradiation shown in FIGS. 1A and 1B.
Figure 13:
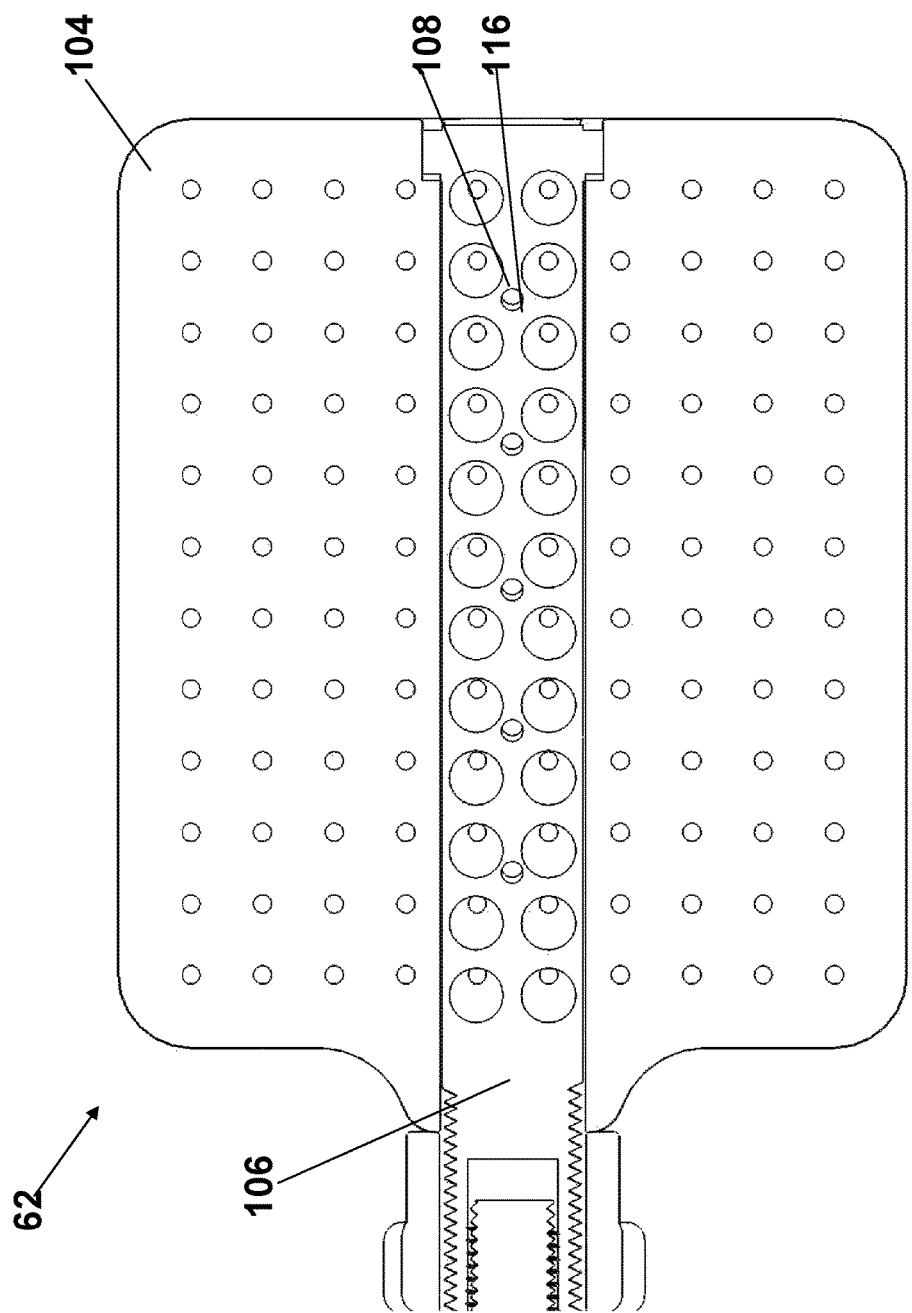
FIG. 13 is a cut-away view of the fiducial needle fixation device in an locked position.

FIGS. 9A and 9B illustrate an example of the locking pin 106 of the template shown in FIGS. 7 and 8 and FIG. 10 illustrate more details the locking pin 106 shown in FIGS. 9A and 9B. The locking pin 106 has the set of outer threads 110 that mesh with the fiducial needle lock 102 to tighten the locking pin from an unlocked position to a locked position as described below. The locking pin 106 may also have a stop 114 that stops the end of the locking pin opposite of the threads 110 and lock it against the end of the template 104 as shown in FIG. 11. The locking pin 106 also comprises one or more fiducial needle holes 116 (located along a center of the locking pin 106 in one implementation as shown in FIG. 9A) that, when the locking pin is in the unlocked position, the one or more fiducial needles pass through the locking pin. When the locking pin is in the locked position (as shown in FIG. 13), the sides of the fiducial needle holes 116 are pressed against the side of the one or more fiducial needles to lock the fiducial needle position relative to the template. The locking pin 106 may also have a plurality of needle holes 118 that are slightly larger in diameter than the fiducial needle holes 116 so that, whether the locking pin 106 is in the locked or unlocked position, the locking pin does not lock the needles at any time. As shown in FIGS. 9B and 10, the locking pin 106 may also include a set of internal threads 112 into which the threads of the attachment ball device 100 are threaded to secure the template and locking pin to the attachment ball device 100.

FIG. 11 illustrates an assembled fiducial needle fixation device 62 that may be used with the mechanism for adjuvant partial breast irradiation shown in FIGS. 1A and 1B. In the assembled state with the locking pin tightened so that the stop 114 is against the side of the template 104 and the fiducial needle lock 102 is tightened and the attachment ball device 100 is secured to the fiducial needle fixation device 62.

Figure 12A:
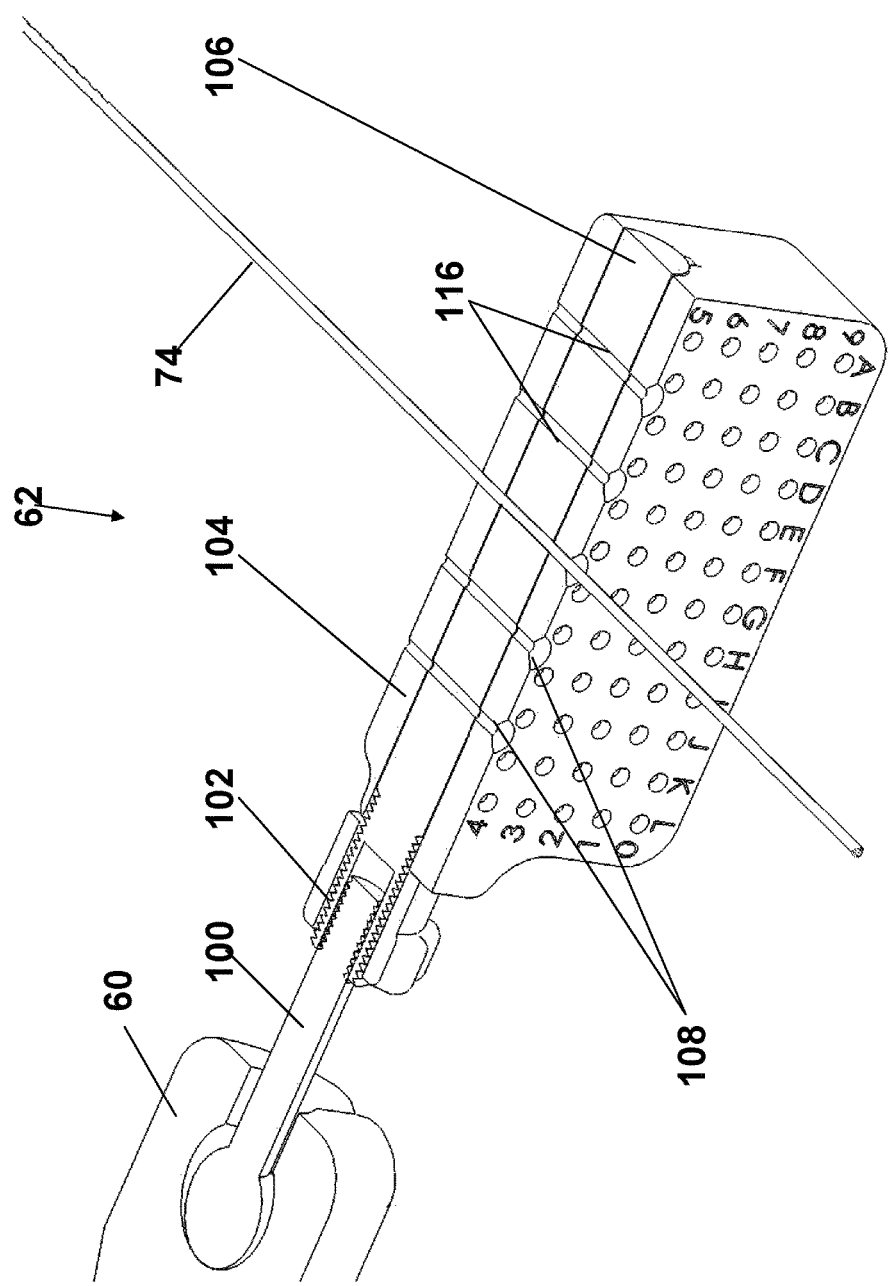
FIGS. 12A and 12B are a cut-away view of the fiducial needle fixation device in an unlocked position.
Figure 12B:
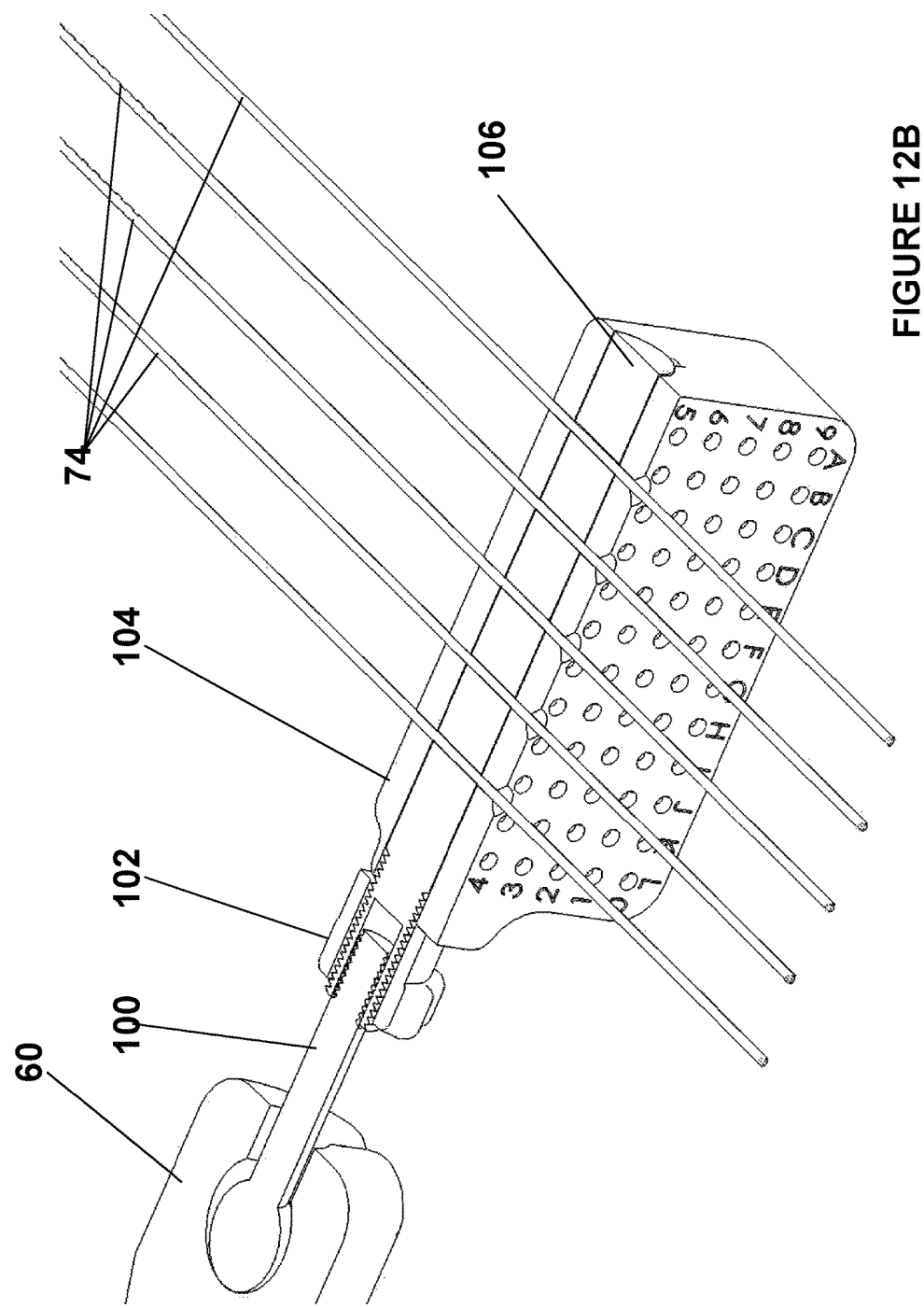

FIGS. 12A and 12B are a cut-away view of the fiducial needle fixation device in an unlocked position for a different number of fiducial needles wherein the template 104 has the locking pin 106 inserted. In the unlocked position as shown in FIGS. 12A and 12B, the fiducial needle locations 108 of the template are aligned with the fiducial needle holes 116 of the locking pin 106 so that the fiducial needle 74 does not have its position locked relative to the template 104 and the fiducial needle can be slid though the template 104 to properly position the fiducial needle relative to the template. FIG. 13 is a cut-away view of the fiducial needle fixation device 62 in an locked position. In the locked position, the locking pin 106 is tightened so that the fiducial needle locations 108 of the template are not aligned with the fiducial needle holes 116 of the locking pin 106 so that the sides of the fiducial needle holes 116 press against the side of a fiducial needle to lock the fiducial needle position relative to the fiducial needle fixation device 62. When the fiducial needle position is locked relative to the fiducial needle fixation device 62, the surgeon can precisely implant radioactive sources into the tissue.

Figure 14A:
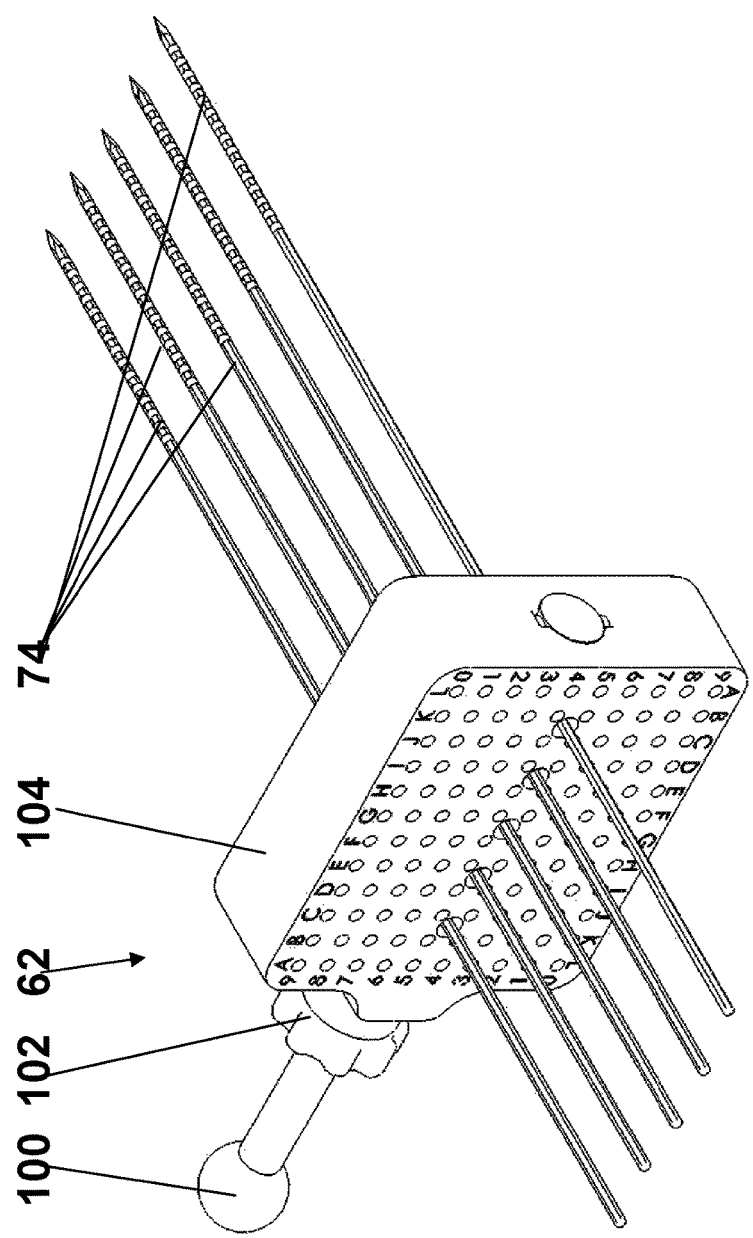
FIGS. 14A-14C illustrate different examples of the fiducial needle fixation device with fiducial needles locked into the fiducial needle fixation device.
Figure 14B:
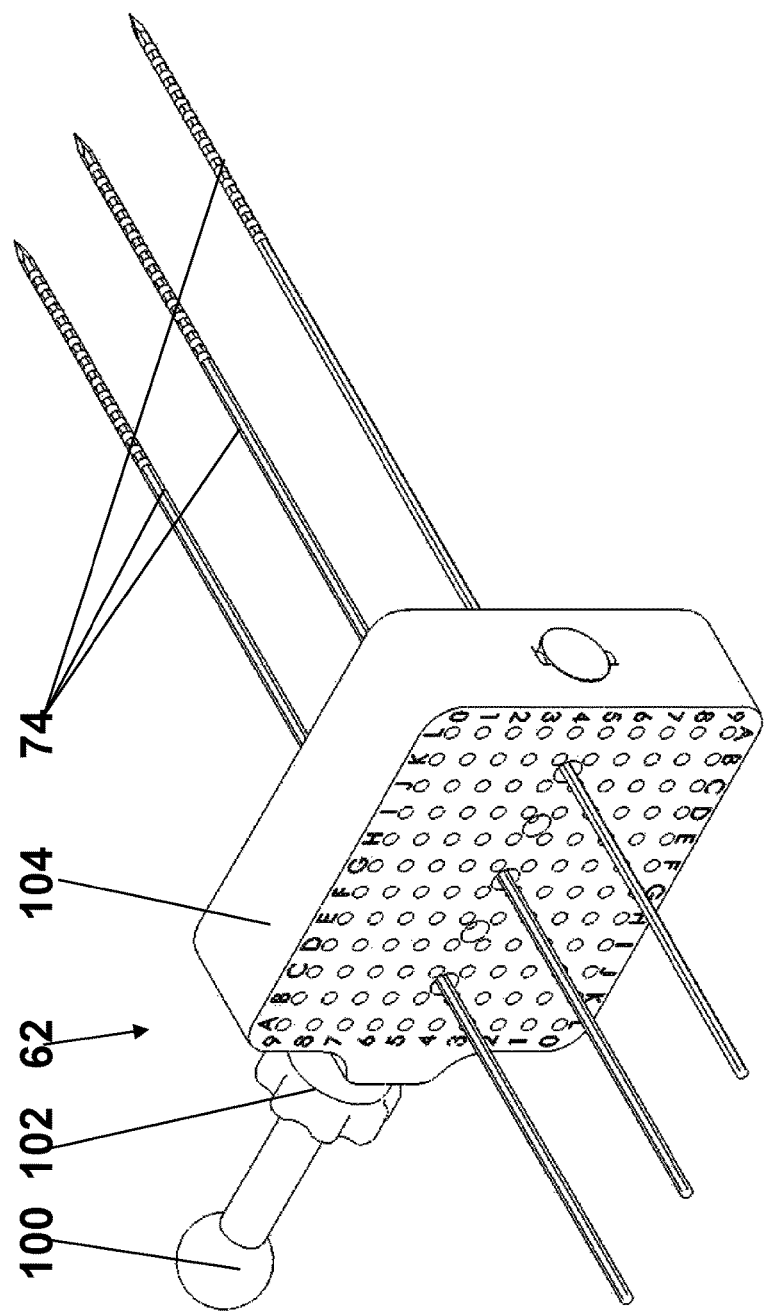
Figure 14C:
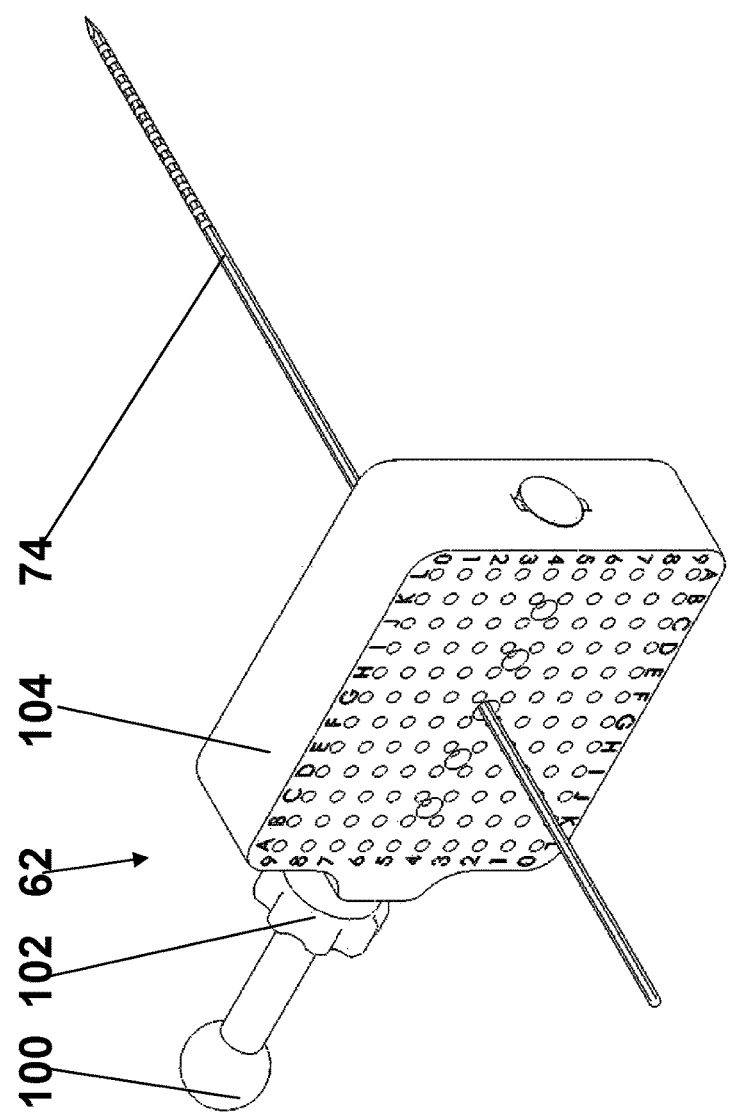

FIGS. 14A-14C illustrate different examples of the fiducial needle fixation device 62 with fiducial needles 74 locked into the fiducial needle fixation device. In particular, the fiducial needle fixation device 62 with four fiducial needles locked into the fiducial needle fixation device, three fiducial needles locked into the fiducial needle fixation device and one fiducial needle locked into the fiducial needle fixation device as shown. Thus, the fiducial needle fixation device permits one or more (up to five in the implementation shown) to be locked into the fiducial needle fixation device. However, the fiducial needle fixation device may also be constructed to allow additional fiducial needles to be positioned and locked into the fiducial needle fixation device.

Figure 15A:
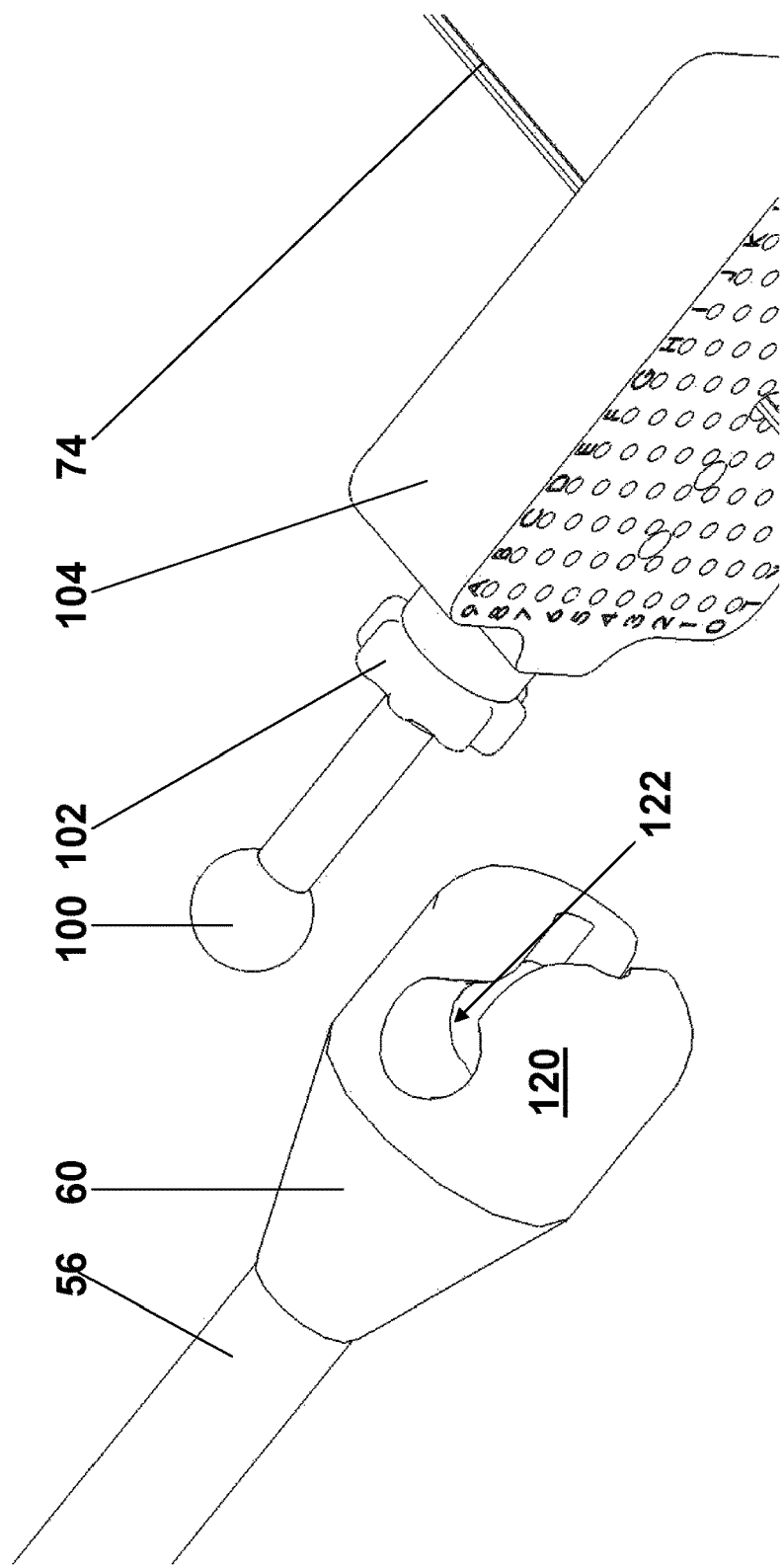
FIGS. 15A-15C illustrate the fiducial needle fixation device with locked fiducial needles being inserted into the engagement device.
Figure 15B:
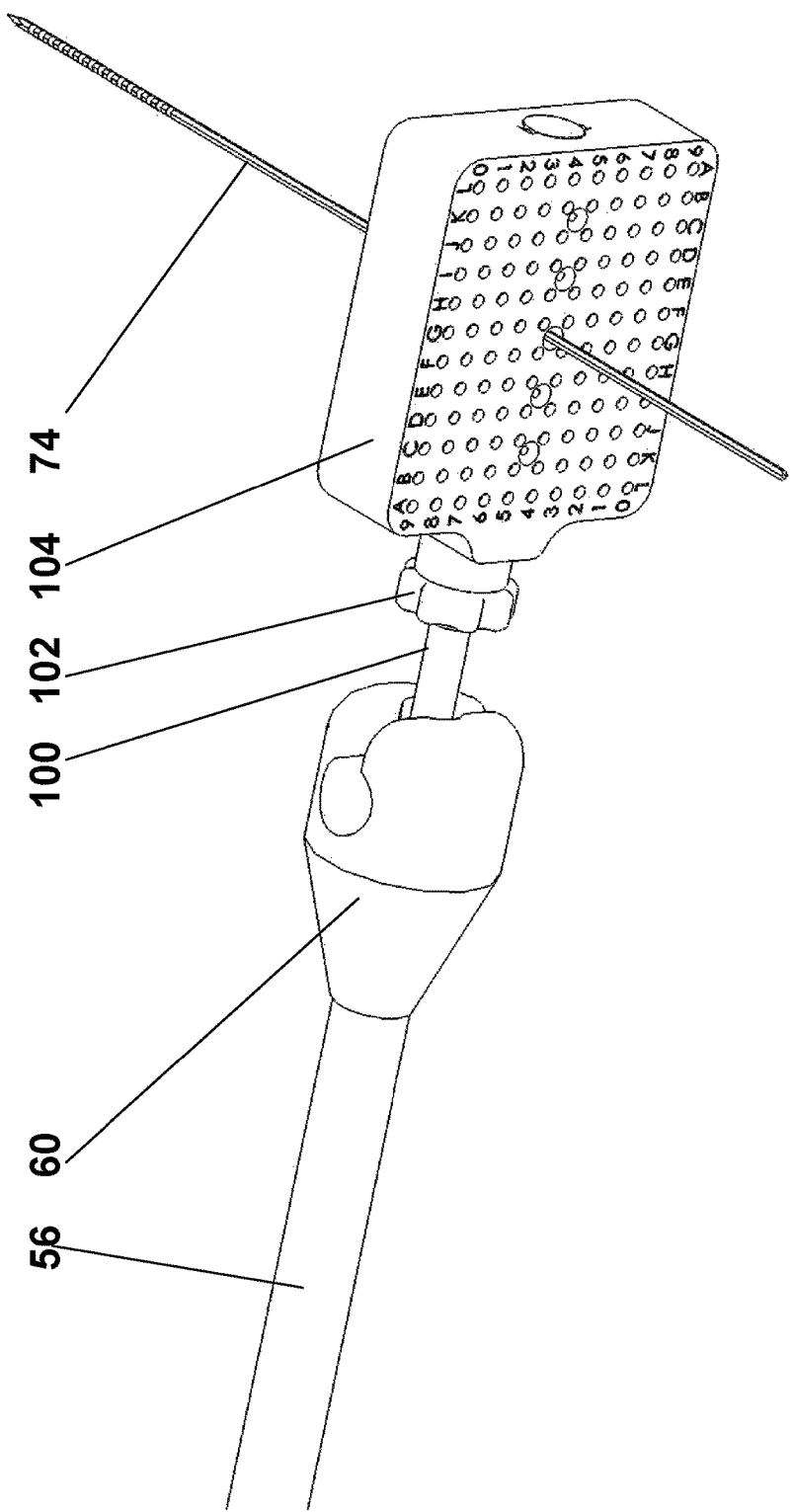
Figure 15C:
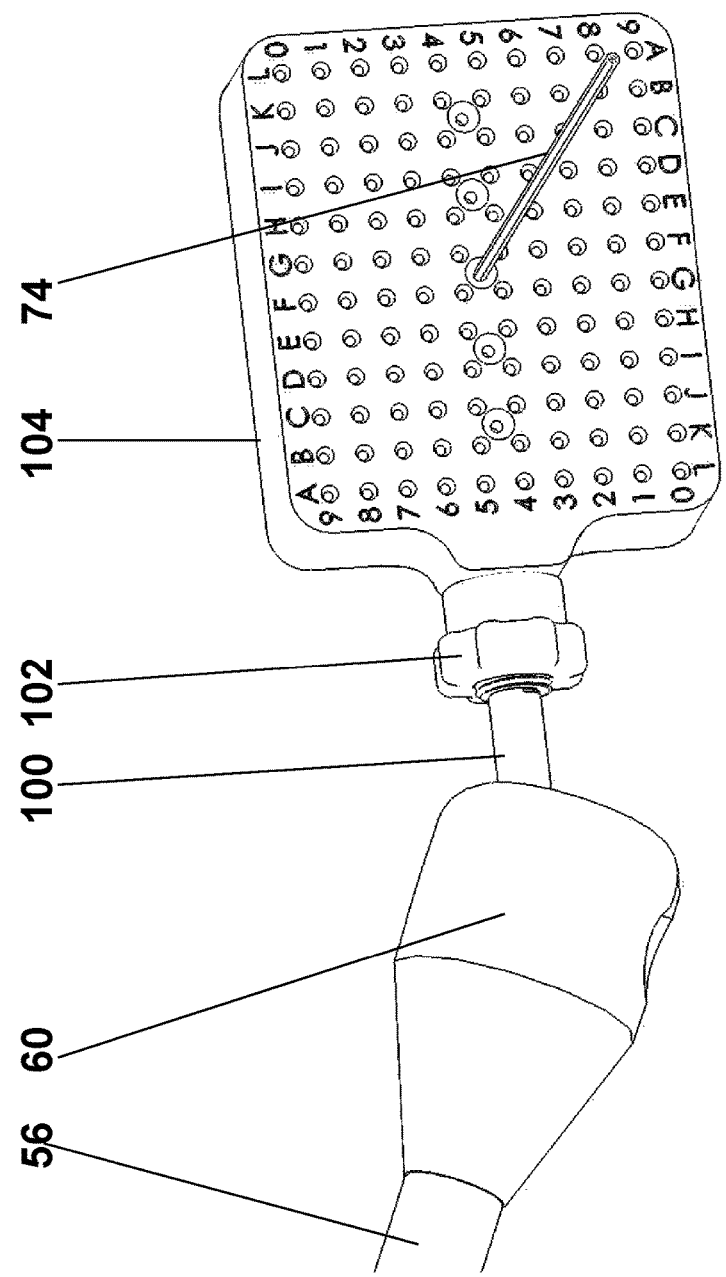

FIGS. 15A-15C illustrate the fiducial needle fixation device 62 with locked fiducial needles 74 being inserted into the engagement device 60. The engagement device 60 may comprise a head portion 120 that is rigidly attached to the stereotactic armature 56 wherein the head portion has a socket region 122. As shown in FIGS. 15A and 15B, the ball of the attachment ball device 100 can be quickly inserted into the socket region 122 to secure the fiducial needle fixation device 62 fixedly to the stereotactic armature 56, but allow the fiducial needle fixation device 62 to also be rapidly removed from the engagement device 60 as needed.

Figure 16:
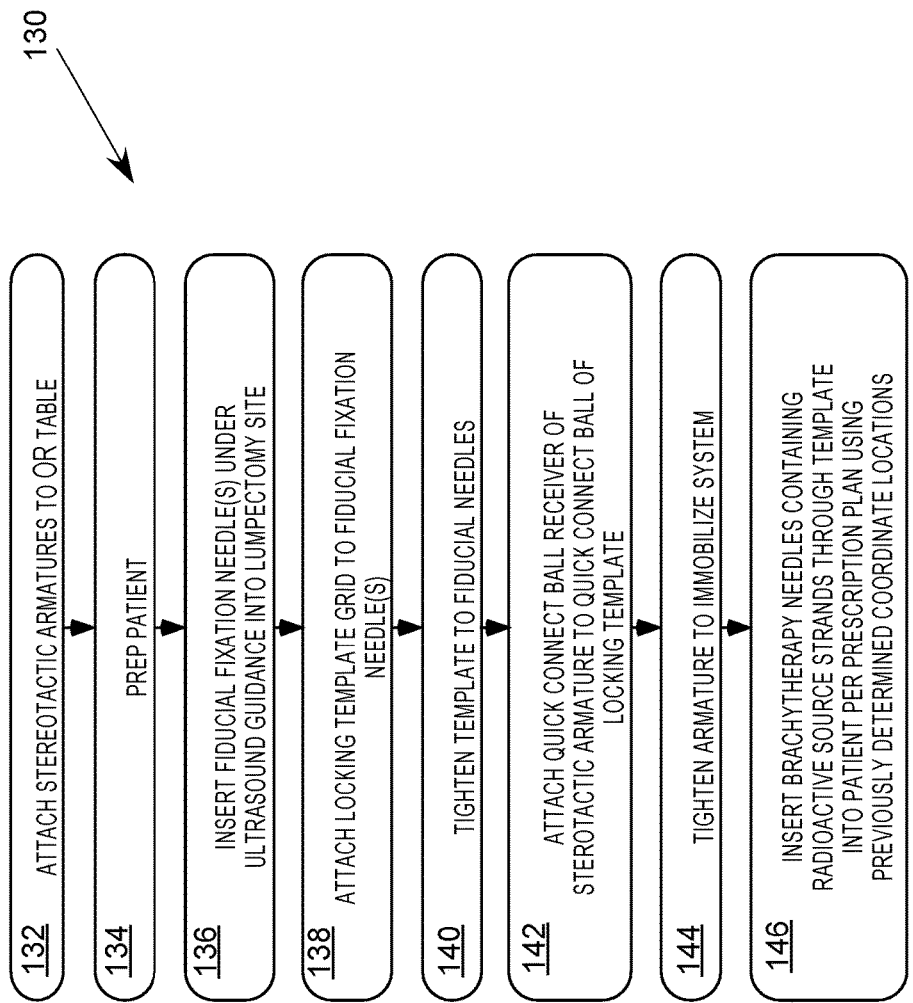
FIG. 16 illustrates a method for adjuvant partial breast irradiation using the fiducial needle fixation mechanisms.

FIG. 16 illustrates a method 130 for adjuvant partial breast irradiation using the fiducial needle fixation mechanisms. The method described can be implemented using the various devices and mechanisms described above and allow the surgeon to precisely implant radioactive sources into the tissue. In a first process 132, the one or more stereotactic armatures are attached to the operating table as shown above in FIGS. 1A and 1B. Then, the patient is prepared for surgery as is well known (134). For adjuvant partial breast irradiation treatment, the patient may have her arm above her head on the side of the breast to be treated. Next, the surgeon or technician inserts one or more fiducial fixation needles, under guidance by a medical imaging technology, into the site (136) such as the lumpectomy site when a breast cancer patient is being treated. Next, the fiducial needle fixation device is attached to the one or more fiducial needles (138) with the fiducial needle fixation device is the unlocked position. For the adjuvant partial breast irradiation, it is desirable to have the fiducial needle fixation device positioned adjacent and touching the breast tissue. Once properly positioned, the fiducial needle fixation device is tightened into the locked position (140). The ball of the assembled and locked fiducial needle fixation device is slipped into the quick connect socket of the stereotactic armature (142) to fix the fiducial needle fixation device with respect to the operating table and the patient. The armatures are then tightened (144) to immobilize the system. Once the system is immobilize (which ensures precise placement of the radioactive sources), the surgeon may begin to insert the brachytherapy needles containing the radioactive sources and/or source strands through the template and into the patient per the previously determined coordinate locations of the prescription treatment plan. Once the implantation of the radioactive sources is completed, the method is completed.

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A device, comprising:
a needle lock that locks at least one fiducial needle relative to a fixed frame of reference, each fiducial needle having a distal end with a surface adapted to locate and fixate tissue into which the at least one fiducial needle is inserted and a sharpened tip portion and a proximal end being inserted through a grid that fixates the at least one fiducial needle to the fixed frame of reference; and
the grid being attached to the needle lock, the grid having a plurality of fiducial needle holes along a longitudinal axis each having a grid needle lock through which the at least one fiducial needle is inserted and locked, a plurality of radioactive source needle holes located above the longitudinal axis and a plurality of radioactive source needle holes located below the longitudinal axis, each radioactive source needle hole does not have a grid needle lock through which a radioactive source needle is capable of being passed into the tissue fixated by the locked at least one fiducial needle.

2. The device of claim 1, wherein the needle lock locks a position of the at least one fiducial needle relative to the grid while allowing the radioactive source needle to freely slide relative to the grid.

3. The device of claim 2, wherein the needle lock further comprises an attachment ball device that threadably attaches to the grid, a fiducial needle lock that attaches to the grid and wherein the grid needle lock is capable of being tightened to lock the position of the plurality of fiducial needles relative to the grid.

4. The device of claim 3 further comprising an engagement device that removably secures the needle lock to the fixed frame of reference.

5. The device of claim 4, wherein the engagement device further comprises a socket portion and wherein the attachment ball device further comprises a ball portion wherein the ball portion is removably inserted into the socket portion to secure the needle lock to the fixed frame of reference.

6. The device of claim 1, wherein the grid further comprises a parallelogram array of the radioactive source needle holes and wherein the plurality of fiducial needle holes are along a center line of the grid.

7. The device of claim 1, wherein each fiducial needle has a surface feature that is visualized.

8. The device of claim 7, wherein the surface feature further comprises a recessed portion and a raised portion along a shaft of each fiducial needle.

9. The device of claim 7, wherein each fiducial needle has a shaft portion and the shaft portion has one of a round cross section, a square cross section, a triangular cross section, a hexagonal cross section and an octagonal cross section.

10. The device of claim 1, wherein the surface of the at least one fiducial needle further comprises one or more user deployable projection that anchors each fiducial needle into the tissue.

11. The device of claim 1, wherein the at least one fiducial needle further comprises one or more depressed regions on the at least one fiducial needle configured to receive tissue.

12. A device, comprising:
a needle lock that locks at least one fiducial needle relative to a fixed frame of reference, each fiducial needle having a distal end with a surface adapted to locate and fixate tissue into which the at least one fiducial needle is inserted and a proximal end being inserted through a grid that fixates the at least one fiducial needle to the fixed frame of reference;
the grid being attached to the needle lock, the grid having a plurality of fiducial needle holes each having a grid needle lock through which the at least one fiducial needle is inserted and locked and a plurality of radioactive source needle holes that do not have a grid needle lock through which a radioactive source needle is capable of being passed into the tissue fixated by the locked at least one fiducial needle; and
wherein the needle lock locks a position of the at least one fiducial needle relative to the grid while allowing the plurality of radioactive source needles to freely slide relative to the grid and further comprises an attachment ball device that threadably attaches the grid, a fiducial needle lock that attaches to the grid and wherein the grid needle lock is capable of being tightened to lock the position of the plurality of fiducial needles relative to the grid, and wherein the grid needle lock further comprises a locking pin having a set of fiducial needle holes through the locking pin wherein a side of each fiducial needle hole is pressed against the at least one fiducial needle passing through the needle lock when the locking pin is in a locked position, a set of radioactive source needle holes through the locking pin, a set of outer threads that cooperate with the fiducial needle lock to move the locking pin between an unlocked position and the locked position, and a set of inner threads that cooperate with the attachment ball device to attach needle lock to the fixed frame of reference.

* * * * *